US012721510B2

(12) United States Patent
Kratuncheva et al.

(10) Patent No.: US 12,721,510 B2
(45) Date of Patent: Sep. 1, 2026

(54) MOTION-STABILIZED BACKGROUND SUBTRACTION FOR FLUORESCENCE IMAGING

(71) Applicant: SurgVision Gmbh, Munich (DE)

(72) Inventors: Gergana Kratuncheva, Munich (DE); Maximilian Koch, Munich (DE); Adrian Taruttis, Munich (DE); Gianpaolo Trotta, Milan (IT); Dario Piloni, Milan (IT); Luca Azzolin, Milan (IT)

(73) Assignee: SurgVision Gmbh, Munich (DE)

( * ) Notice: Subject to any disclaimer, the term of this patent is extended or adjusted under 35 U.S.C. 154(b) by 0 days.

(21) Appl. No.: 19/143,522

(22) PCT Filed: Dec. 18, 2023

(86) PCT No.: PCT/EP2023/086478
§ 371 (c)(1),
(2) Date: Jun. 26, 2025

(87) PCT Pub. No.: WO2024/141319
PCT Pub. Date: Jul. 4, 2024

(65) Prior Publication Data
US 2026/0215666 A1 Jul. 30, 2026

(30) Foreign Application Priority Data
Dec. 30, 2022 (EP) .................................... 22217286

(51) Int. Cl.
*A61B 1/04* (2006.01)
*A61B 1/00* (2006.01)
*A61B 1/06* (2006.01)

(52) U.S. Cl.
CPC ........ *A61B 1/043* (2013.01); *A61B 1/000095* (2022.02); *A61B 1/0638* (2013.01)

(58) Field of Classification Search
CPC .. A61B 1/043; A61B 1/000095; A61B 1/0638
See application file for complete search history.

(56) References Cited

U.S. PATENT DOCUMENTS 11,322,245 B2 5/2022 Michihata
2003/0219150 A1 * 11/2003 Niles ......................... G06T 7/74 382/128

(Continued)

FOREIGN PATENT DOCUMENTS

JP 6931705 B2 9/2021

OTHER PUBLICATIONS

International Search Report and Written Opinion for International Patent Application No. PCT/EP2023/086478, mailed Mar. 14, 2024, 13 pages.

*Primary Examiner* — Bo Joseph Peng
(74) *Attorney, Agent, or Firm* — Withrow & Terranova, PLLC

(57) ABSTRACT

A method (300) at an imaging acquisition system (100), comprising: obtaining a sequence of reflectance images (401-406); acquiring a sequence of fluorescence channel images (601-603) including light images (602), acquired while using a light source to cause a target body-part to emit fluorescent light, alternating with dark images (601, 603), acquired without using the light source; determining (304, 310) a first reflectance image (401) associated with a first fluorescence channel image (601) having a first reference time, and a second reflectance image (403) associated with a consecutive second fluorescence channel image (602) having a second reference time; determining (311) a transformation matrix based on a relative alignment of the first and second reflectance images; applying (315) the transformation matrix to one of the first and second fluorescence channel images to align these images; performing a subtraction (316) between the fluorescence channel image to which (Continued)

the transformation matrix has been applied and the other image to obtain a background-subtracted image; and outputting the background-subtracted image for displaying.

21 Claims, 7 Drawing Sheets

(56) References Cited

U.S. PATENT DOCUMENTS

| | | | | |
|---|---|---|---|---|
| 2022/0087518 | A1* | 3/2022 | Walle-Jensen | A61B 1/043 |
| 2022/0366708 | A1 | 11/2022 | Van Der Horst | |
| 2023/0301520 | A1* | 9/2023 | Bukesov | A61B 1/00059 |

* cited by examiner

MOTION-STABILIZED BACKGROUND SUBTRACTION FOR FLUORESCENCE IMAGING

This application is a 35 USC 371 national phase filing of International Application No. PCT/EP2023/086478, filed Dec. 18, 2023, which claims priority to EP Application Serial No. 22217286.8, filed Dec. 30, 2022, the disclosures of which are incorporated herein by reference in their entireties.

TECHNICAL FIELD

The present disclosure relates to background subtraction applied in fluorescence imaging.

BACKGROUND

Fluorescence imaging is a specific imaging technique that is used to acquire images providing a visual representation of target objects, even if they are not visible directly. This technique is based on a fluorescence phenomenon, consisting of the emission of light by fluorescent substances when subject to excitation light (having wavelength and energy sufficient to excite the fluorophores of the fluorescent substances). For this purpose, fluorescence images are generally acquired and displayed to represent the fluorescent light that is emitted from different locations corresponding to the fluorophores that are present in the target object.

Fluorescence imaging is routinely exploited in Fluorescence Guided Surgery (FGS) (and particularly Fluorescence Guided Resection (FGR) when relating to tumors), endoscopy and other medical (surgical/diagnostic/therapeutic) procedures for identifying a desired target within inspected (inner) body-parts of patients (such as lesions like tumors).

For this purpose, a fluorescent agent is generally administered to a patient to reach a desired organic target within the body-part to be inspected, and attach to the target. For example, in Fluorescence Molecular Imaging (FMI) applications, the fluorescent agent is adapted to reach specific molecules of desired targets, such as lesions like tumors, and then remain immobilized on the specific molecules.

Then, an excitation light source is used to illuminate the body part under inspection to cause the fluorescent agent administrated to the patient to emit fluorescent light that is captured, using a fluorescence camera, so as to acquire a sequence of fluorescence images ("light images", acquired using the excitation light source) showing the locations, within the inspected body-part, of the emitting fluorescent agent (and therefore of the desired target).

The sequence of light images acquired using the fluorescence camera can be displayed on a monitor together with a sequence of corresponding color images of the inspected body-part, separately acquired using a color camera, so as to show to an operator the target object juxtaposed to the surrounding regions of the inspected body-part. For example, in surgical operations the displayed images can assist a surgeon for recognizing the margins of a lesion to be resected, in diagnostic applications can assist a doctor for discovering or monitoring the lesions, and in therapeutic applications can assist a physician for delineating the lesions to be treated.

However, the image content of the light images acquired using the fluorescence camera may not be limited to image content corresponding to the emission of fluorescent light from the fluorescent agent in response to the light provided by the excitation light source, and indeed may include spurious image content due to any ambient light different than the excitation light and the fluorescent light emitted by the fluorescent target in response to the excitation light, but having some spectrum components falling within the passband of the fluorescence camera. A known technique for eliminating this spurious contribution, disclosed e.g., in Themelis et al., Journal of Biomedical Optics 2009, as subtraction of the "dark image", is background subtraction.

According to this technique, the fluorescence camera is used to acquire a sequence of images ("dark images") without using the excitation light unit to cause the fluorescent agent to emit fluorescent light, in an alternate way relative to the acquisition of the light images (acquired using the excitation light to cause the fluorescent agent to emit fluorescent light). In this way, the acquired dark images include background image content due to the ambient light falling within the bandpass of the fluorescence camera and as such, the acquired dark images can be subtracted from corresponding previously or consequently acquired light images to obtain background-subtracted fluorescence images (where the spurious background content included in the light images due to the ambient light is ideally removed). In practice, assuming that the background image content of an acquired dark image perfectly matches the spurious background image content included in the acquired light image, the subtraction of the dark image from the light image will remove this spurious content from the obtained background-subtracted fluorescence image.

The background-subtracted fluorescence images so obtained can then be displayed, e.g., in a live video of fluorescence images.

However, this background subtraction method has some drawbacks in practice. In particular, a movement of one or more objects within the field of view of the fluorescence camera (e.g., the body-part under inspection or another object, e.g., a surgical instruments or hand) and/or a movement of the fluorescence camera relative to the captured scene can occur between the acquisition times of a dark image and a light image, causing a mismatch (misalignment) between the background image content of the dark image and corresponding background image content in the light image. This misalignment (even of a small amount-like a single pixel shift) can cause the presence of non-negligible artifacts in the background-subtracted image. For example, a lateral shifting of an object reflecting ambient light within the field view (e.g., a white light used to acquire the color images, an artificial light illuminating the room where the medical operation is performed, or sunlight penetrating into the room), occurring between the acquisition times of a dark image and a consecutive light image, would result in the edge of the imaged object being represented by high intensity values within the obtained background-subtracted image. As such, ambient light with a non-negligible intensity relative to the intensity of the emitted fluorescent light can cause, in combination with object/camera motion, non-negligible ambient light artifacts in the background-subtracted images. The greater the ambient light intensity, the greater is the intensity value of the artifacts.

Moreover, the ambient light can cause spurious (background) fluorescence emission from endogenous fluorophores of the inspected body part other than the fluorophores of the fluorescent agent (not caused by using the excitation light unit) that in combination with object/camera motion can lead to artifacts in the portions of the background-subtracted images, where the background fluorescence is shifted due to the target object movement.

Another problem in relation to the presence of a strong ambient light is that the image sensor of the fluorescence camera has a finite dynamic range. As such, the sensor can be saturated (overexposed) in case of too much incident light (especially in the case of ambient light emitted from artificial light illuminating the room or sunshine, passing within the fluorescence detection passband, since the magnitude of this light is potentially much greater than the levels of fluorescence emission to be detected by the sensor). However, if only the background-subtracted fluorescence images are displayed to a user, the over-exposure occurring in acquired dark and light images might be not noticeable to the user, since the background subtracted images will not appear brighter than they should under normal exposure. This is because the high saturated values of corresponding pixel areas affected by over-exposure are subtracted from each other during the generation of the background subtracted images, resulting in low intensity (ideally null) pixel values.

Both the above discussed drawbacks have in common that their occurrence is somewhat hidden from the user, because only the background-subtracted images are displayed without directly revealing overexposure (the high pixel values are subtracted away) or motion. These above drawbacks represent real challenges to the practical implementation of background subtraction in live fluorescence imaging.

U.S. Pat. No. 11,322,245 discloses a medical image processing apparatus connected to an observation imager configured to generate a subject image by capturing the light reflected from a subject at a first timing and generate a fluorescent image by capturing fluorescent light emitted from the subject at a second, different, timing. In particular, the medical image processing apparatus is configured to: determine whether at least one of the subject and the observation imager moves between the acquisition of a previous subject image and the first timing or between the acquisition of a previous fluorescent image and the second timing; and prohibit the superimposition of the subject image and the fluorescent image in response to determining a motion of at least one of the subject and the observation imager between the acquisition of the subject images or between the acquisition of the fluorescent images.

U.S. Pat. No. 11,276,148 discloses a method including actuating an emitter to emit a plurality of pulses of electromagnetic radiation (including red, green, blue and fluorescence pulses), and sensing reflected electromagnetic radiation resulting from the plurality of pulses with a pixel array of an image sensor to generate a plurality of exposure frames (including red, green, blue and fluorescent frames). The method further includes detecting motion across two or more sequential exposure frames of the plurality of exposure frames, compensating for the detected motion, and combining the two or more sequential exposure frames to generate an image frame. CN102361583 discloses an image processing device including a motion vector arithmetic unit and an alignment processing unit. The motion vector arithmetic unit is configured to calculate information relating to a motion vector between a fluorescent image of a region being observed (based on the fluorescence generated from the region being observed irradiated with exciting light) and a reflected light image of the region being observed (based on the reflected light from the region being observed). The alignment processing unit is configured to correct the displacement of a subject between the fluorescent image and the reflected light image of the region being observed on the basis of the information relating to the motion vector.

U.S. Pat. No. 10,869,645 discloses an adaptive imaging method for generating low light video of an object for medical visualization, including: acquiring, with an image acquisition assembly, a sequence of reference frames and/or a sequence of low light video frames depicting the object; assessing relative movement between the image acquisition assembly and the object based on at least a portion of the acquired sequence of reference video frames or the acquired sequence of low light video frames; adjusting a level of image processing of the low light video frames based at least in part on the relative movement between the image acquisition assembly and the object; and generating a characteristic low light video output from a quantity of the low light video frames, wherein the quantity of the low light video frames is based on the adjusted level of image processing of the low light video frames.

U.S. Pat. No. 10,108,844 discloses an imaging subsystem configured to image, at different wavelength bands, particles disposed within the subsystem, wherein the imaging subsystem comprises: selecting a first set of one or more optical filters corresponding to a first wavelength band; illuminating the particles through the first set of optical filters; selecting a second set of one or more optical filters corresponding to a second wavelength band; and illuminating the particles through the second set of optical filters; storing data acquired for multiple images of the particles; generating a first composite image of the multiple images, wherein the first composite image includes first composite spots corresponding to the particles, the first composite spots having a first amount of misalignment from the spots in the multiple images of the stored multiple images; and modifying coordinates of at least one of the multiple images such that a second composite image based on the modified coordinates includes second composite spots having a second, smaller, amount of misalignment from the spots in the multiple images.

SUMMARY

According to a first aspect of the present invention there is provided a method according to claim 1.

There are also provided related image acquisition system and computer program product according to claims 17-18 as well as related surgical, diagnostic and therapeutic methods according to claims 19-21.

Embodiments of the invention are based on the appreciation that, although two consecutive dark and light fluorescence channel images (frames) acquired by an imaging acquisition over a fluorescence channel cannot be compared to extract a transformation matrix estimating an amount of motion causing a misalignment between these images (because they have different and little image content: indeed the light image includes image content corresponding to a target body-part emitting fluorescent light in response to excitation light, whereas the dark image includes background content due to a small portion of ambient light passing through the passband of the fluorescence camera), a relative alignment between reference reflectance (e.g., color) images associated with the dark and light images can be instead used to extract a transformation matrix estimating the amount of motion causing a misalignment between the dark and light images.

The transformation matrix can be advantageously applied to correct motion by spatially aligning the dark and light image frames before performing a pixel-wise subtraction of the dark image from the light image. In this way, a motion-stabilized background-subtracted fluorescence image is obtained where the presence of background due to ambient light (other than fluorescent light-emitted in response to excitation light- and the excitation light) is minimized while avoiding artifacts due to motion.

In some of the embodiments where the fluorescence channel and reflectance images are asynchronously acquired, a first interpolated transformation matrix and a second interpolated transformation matrix (suitable for aligning the reference reflectance images to the respective dark and light images) are determined. In some of these embodiments, the transformation matrix to align the dark and light images is determined as a function of the reference reflectance images and the first and second interpolated transformation matrixes. In other of these embodiments, the first and second interpolated transformation matrixes are applied to the reference reflectance images to obtain, respectively, a first virtual reflectance image approximatively aligned to the dark image and a second virtual reflectance image approximatively aligned to the light image. The transformation matrix to align the dark and light images is then determined as the transformation matrix to align the first and second virtual reflectance images. In other of these embodiments, the first and second interpolated transformation matrixes are applied to align the dark and light images to the respective reference reflectance images. The transformation matrix to align the dark and light images is then determined as the transformation matrix to align the reference reflectance images.

In some other embodiments where the fluorescence channel and reflectance images are asynchronously acquired, the reference reflectance images associated to the dark and light images correspond to the reflectance images acquired closest in time to reference times of the dark and light images. The transformation matrix to align the dark and light images is determined as the transformation matrix to align these selected reflectance images.

In some of the embodiments where the fluorescence channel and reflectance images are synchronously acquired, the reference reflectance images associated with the dark and light images correspond to reflectance images acquired at the reference times of the dark and light images. The transformation matrix to align the dark and light images is determined as the transformation matrix to align these selected reflectance images.

In some of the embodiments, after acquisition of either a dark or light image, a check is performed to determine whether the acquired image is overexposed. In response to determining overexposure, a warning is output to signal excess ambient light.

BRIEF DESCRIPTION OF THE DRAWINGS

Embodiments of the invention will now be described, by way of example, with reference to the accompanying drawings, in which.

DESCRIPTION OF THE EMBODIMENTS

Figure 1:
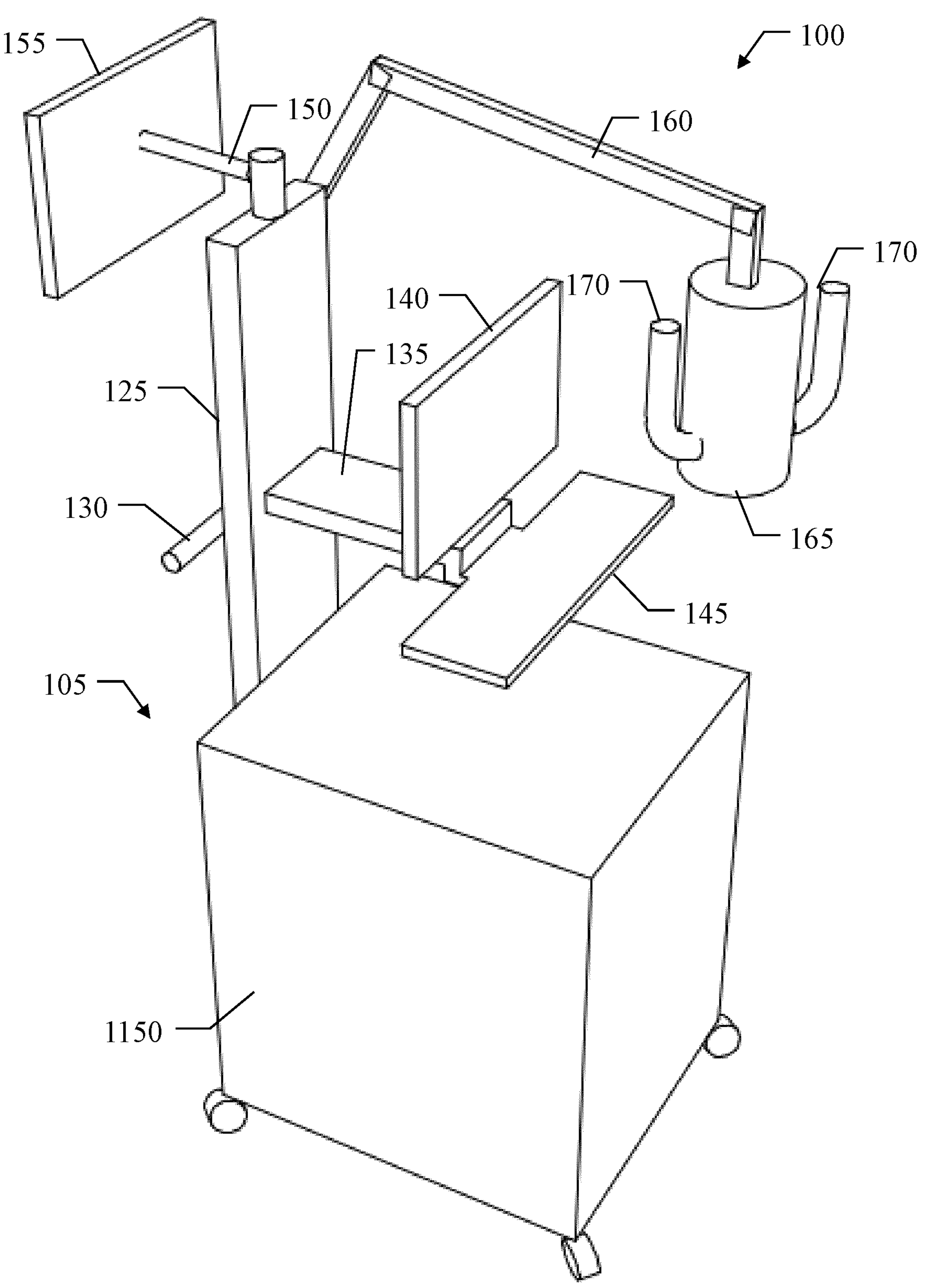
FIG. 1 illustrates an imaging acquisition system for fluorescence-guided open surgery, configured to operate motion-stabilized fluorescence background subtraction according to an embodiment of the present invention.

FIG. 1 illustrates an imaging system 100 for assisting a surgeon in Fluorescence Guided Surgery (such as Fluorescence Guided Resection, if the surgical operation relates to tumors). In particular, the illustrated system 100 comprises an apparatus 105 including a trolley 1150 housing a supply unit and a control unit (not visible in FIG. 1) for supplying and controlling, respectively, the operation of the imaging system 100. A pillar 125 extends upwards from a back surface of the trolley 1150. The pillar 125 has a handlebar 130 for moving the apparatus 105 by an operator. A cantilever 135 projects from the pillar 125, above the trolley 1150. A primary monitor 140 (for displaying images to the operator) and a keyboard 145 with a pointing device such as a mouse or a trackball (for entering information/commands by the operator) are mounted on the cantilever 135. A pivoting arm 150 is mounted on top of the pillar 125 (above the cantilever 135). A secondary monitor 155 (for displaying images to a doctor, such as a surgeon) is mounted on the pivoting arm 150 (so as to allow turning it in either directions). An articulated arm 160 is mounted on top of the pillar 125 as well (next to the pivoting arm 150). An imaging head 165 is suspended from the articulated arm 160. The imaging head 165 is provided with two handlebars 170 (for moving the imaging head 165 by the operator).

Figure 2:
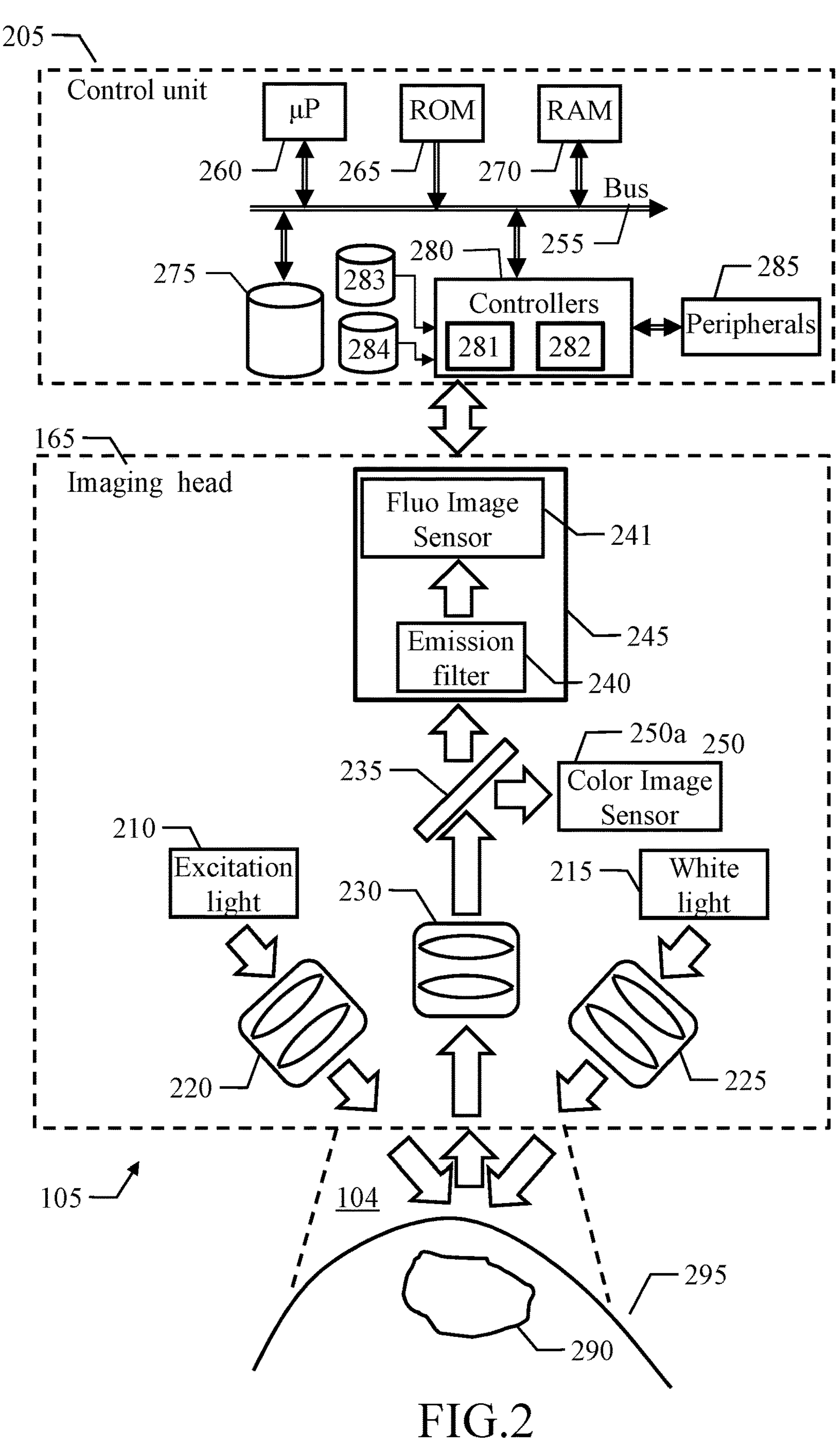
FIG. 2 illustrates a block diagram of the imaging acquisition system illustrated in FIG. 1.

With reference now to FIG. 2, there is schematically illustrated the functional structure of the imaging head 165 and of the control unit (denoted with the reference 205).

The imaging head 165 includes at least an image acquisition unit, for acquiring images of a scene within a corresponding field of view 104 (e.g., a part of the world within a solid angle to which the acquisition unit is sensitive), and an illumination unit configured for illuminating the scene.

In particular, as illustrated in FIG. 2, the imaging head 165 is positioned in operation relative to the body 295 of a patient undergoing a surgical procedure, in such a way that a target body-part 290, exposed by a surgical cavity (for example, a small skin incision in minimally invasive surgery), falls within the field of view 104 of the image acquisition unit. In operation, the field of view 104 may also contain one or more extraneous objects different from the surgical cavity (not shown in FIG. 2), for example, surgical instruments, hands, surgical tools, surrounding body-parts, background materials and so on (either around or overlapping the surgical cavity). The target body-part 290 includes a fluorescent substance. For this purpose, a fluorescent agent is administered to the patient (for example, intravenously or locally). The fluorescent agent can be a target-specific fluorescent agent that is adapted to attaching to a specific biological target (such as tumoral tissues, nerves, blood-vessels, lymph-nodes, lymph-vessels and so on). The fluorescent agent is administered to the patient 295 in advance, so as to allow the fluorescent agent to circulate within a vascular system of the patient 295 until reaching the body-part 290 and attaching to the desired target.

The illumination unit and the image acquisition unit of the imaging head 165 are now disclosed in more detail.

Starting from the illumination unit, it includes a Near-infra red (NIR) excitation light source 210 (e.g. a laser or LED source) configured to emit excitation light that is delivered, by corresponding delivery optics 220, to the scene within the field of view 104 of the image acquisition unit. The NIR excitation light has wavelength and energy suitable for exciting the fluorophores of the fluorescent substance in the target body-part 290 so as to cause the emission of fluorescent light. In particular, upon absorbing the excitation light, the fluorophores pass to an excited, unstable, (electronic) state, and very shortly after reaching the unstable electronic state decay to a ground (electronic) state, thereby emitting the fluorescent light with an intensity depending on an amount of the fluorophores that are illuminated (and other factors including the fluorophores position within the field of view 104 and the body-part 290) and with a characteristic NIR emission spectrum (having characteristic wavelengths longer than the wavelengths of the NIR excitation light, because of the energy dissipated as heat in the excited state).

The illumination unit further includes a white light source 215 (for example, a LED, halogen, or Xenon lamp) configured to emit white light (i.e. a light containing all the wavelengths of the color spectrum that is visible to the human eye at equal intensity, so as to appear substantially colorless to the human eye) that is delivered, by corresponding delivery optics 225, to the scene within the field of view 104 of the image acquisition system.

Moving to the image acquisition unit, it comprises collection optics 230 configured to collect light present within the field of view 104. The collected light present in the scene can comprise: fluorescent light that is emitted by the fluorophores present in target-body part 290 (in response to absorbing the excitation light provided by the light source 210); any spurious fluorescent light that can be emitted by fluorophores other than the fluorophores of the target fluorescent agent, such as endogenous fluorophores present within the inspected body-part 290 (in response to absorbing some components of the white light provided by the light source 215 or of other ambient light); excitation light reflected by any object present in the field of view 104; and visible light that is reflected by any object present in the field of view 104 (illuminated by the white light emitted by the light source 215 or by any other visible light present in the room where the imaging system 100 is operating, e.g., an artificial room light, the light emitted from the monitors 140, 150, sunlight penetrating into the room, and so on).

The image acquisition unit further comprises a beam-splitter 235 configured to split the collected light within the field of view 104 into two channels, namely a first channel of collected light within a NIR spectrum (including the fluorescence emission spectrum) and a second channel of collected light within the visible light spectrum. For example, the beam-splitter 235 can be a dichroic mirror transmitting and reflecting the collected light at wavelengths above and below, respectively, a threshold wavelength between the NIR and the visible light spectrum.

The acquisition unit further comprises a fluorescence camera 245 with a fluorescence emission detection passband. In particular, the fluorescence camera 245 includes a fluorescence image sensor 241 and an associated emission filter 240 (e.g., positioned on or close to a sensing surface of the sensor 241).

The filter 240 is a passband filter having a fluorescence detection passband corresponding to the fluorescence emission spectrum of the fluorophores in the target body-part 290. The filter 240 can be formed by a single filter or by a combination of a plurality of filters. As such, the filter 240 is configured to filter the light provided by the first channel of the beam-splitter 235, so as to allow the passage therethrough (towards the sensing surface of the sensor 241) of light within the fluorescence emission spectrum of the target fluorophores, while preventing the passage therethrough (in ideal operation) of any components of the excitation light reflected by objects within the field of view 104 or any reflected ambient light different than the fluorescent light and the excitation light (including e.g., any portions of the reflected white light emitted by the white light source 215 or of other artificial lights illuminating the room where the system 100 is operated, or sunlight portions penetrating into the room, that can fall within the NIR spectrum or have been wrongly deviated towards the filter 240 due to non-ideal operation of the beam-splitter 235).

The image sensor 241 can be any sensor having a suitable sensitivity for detecting incident light emitted by the fluorophores in the target body-part 290 (provided by the second channel of the beam-splitter 235 and passing through the filter 240). In response to this light detection, the fluorescence camera 245 is configured to generate fluorescence images representing the distribution of the fluorophores in the field of view 104. For example, the sensor 241 can be an EMCCD sensor, an Intensified CCD, ICCD, sensor, a CMOS sensor, an InGaAs sensor, a photomultiplier tube (PMT), or any other high-sensitive sensor for low-light imaging in NIR. With reference back to the second channel of the beam-splitter 235, collecting the reflected visible light within the field of view 104, the image acquisition unit of the imaging head 165 further includes a reflectance camera, in particular a color camera 250 including an image sensor 250*a* (e.g., of the CCD or CMOS type) capable of separately detecting the intensity of color components of the reflected visible light provided by the second channel of the beam-splitter 230.

For example, the image sensor 250*a* can include a RGB filter (e.g., a Bayer filter) disposed on its sensing surface (allowing, respectively, red, green and blue components of the collected white light to reach respective filtered pixel areas of the sensor surface). In some variations, the image sensor may have in addition to RGB sensors or instead of RGB sensors, either pixels which are sensitive to only a band of light or for example a broadband, such as the visible light spectrum, referred to herein as white (W) pixels. (In still further variations, the image sensor can comprise a hyperspectral sensor with separate planes sensitive to sub-bands of red, green or blue light). Other image sensors include for example, sensors with a color filter array (CFA) other than an RGB filter, e.g., an RGBE filter (similar to a Bayer filter but with added "emerald" filters), or a CYYM filter (having an array of cyan, yellow and magenta filters). Furthermore, instead of using a CFA, the image sensor can be manufactured in such a way as to include by itself areas with different sensitivity to the different color components of the incoming light, or an arrangement can be employed whereby the incoming light is split into a plurality of color components each directed towards a corresponding sensor surface.

With reference now to the control unit 205 of the imaging system 100, it comprises several units that are connected to each other through a bus structure 255 (as schematically illustrated in FIG. 2). In particular, the unit 205 comprises one or more microprocessors (μP) 260 configured to provide processing and coordination functionalities of the control unit 205. A non-volatile memory (ROM) 265 stores basic code for a bootstrap of the control unit 205 and a volatile memory (RAM) 270 is used as a working memory by the microprocessors 260. The control unit 205 is further provided with a mass-memory 275 for storing programs and data (for example, a Solid-State-Disk, or SSD).

Moreover, the control unit 205 comprises a number of controllers 280 for peripherals, or Input/Output (I/O) units. In particular one or more of the controllers 280 are configured to control peripherals 285, such as the primary and secondary monitors 140, 155, the keyboard 145, the pointing device, a drive for reading/writing removable storage units (such as of USB type), and a network interface card (NIC) for connecting to a communication network (such as a LAN and then the Internet).

Furthermore, the controllers 280 include a fluorescence imaging control module 281 and a color imaging control module 282 which are configured to control the operation of the excitation light source 210, the white light source 215, the fluorescence camera 245 and the color camera 250 of the imaging head 165 in order to acquire sequences of fluorescence and color images.

Figure 4:
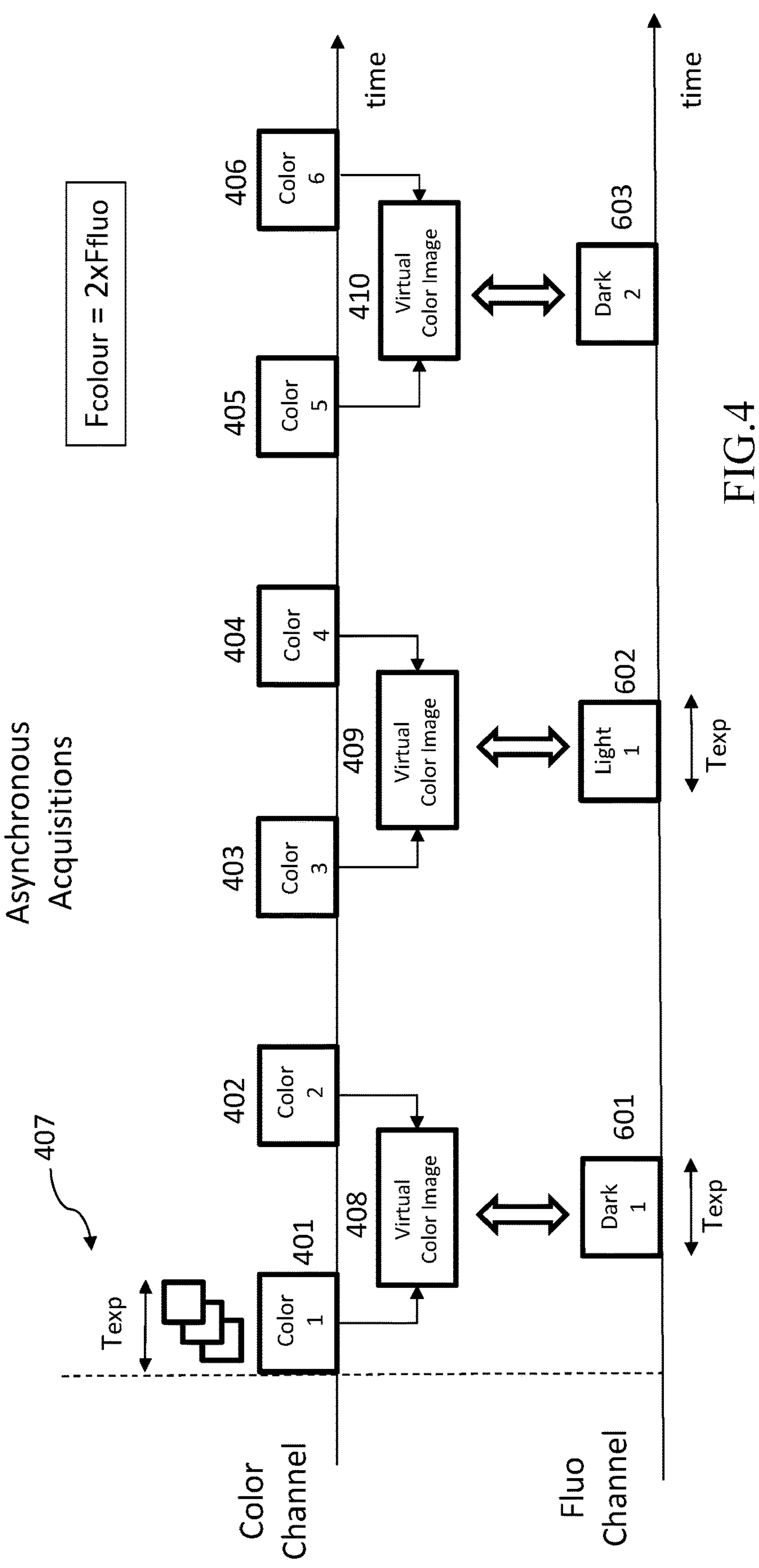
FIG. 4 illustrates a sequence of color images and dark and light images acquired asynchronously over time, with reference virtual color images assigned to the dark or light images according to the operation of an embodiment of the method of FIG. 3.

In particular, the fluorescence imaging control module 281 is configured to coordinate the operation of the fluorescence camera 245 and the turning on/off of the excitation light source 210 so as to acquire over a fluorescence acquisition channel:

- a sequence of images including light images (including for example the light image 602 illustrated in FIG. 4) acquired while using the light unit 210 to cause the fluorescent substance in the target body-part 209 to emit fluorescent light, alternating with
- a sequence of dark images (including for example the dark images 601 and 603 illustrated in FIG. 4) acquired without using the excitation light source 210.

The acquired alternating dark and light images have the same size and shape and can comprise a matrix of cells each storing the intensity value of a pixel, i.e., a basic picture element corresponding to a location of the field of view 104. As such, each pixel value defines the brightness of the pixel as a function of an intensity of the light emitted by the corresponding location (and then, in the light images, of an amount of the fluorescent agent present therein—for example, from black to white as the amount of the fluorescent agent increases).

Preferably, the acquired dark and light images are monochrome images comprising gray-scale values. Alternatively, the acquired light and dark images can be defined with values of other types (e.g., colors value in RBG, YcBcr, HSL, CIE-L*a*b, LAB color and the like representations, for pixels or voxels, and so on).

Moreover, in order to acquire the light images during an exposure time, $T_{exp}$, suitable for allowing a proper exposure level of the light images (e.g., allowing a certain average level or range of brightness, within the exposure range of the image sensor 241, over a certain number of pixels in the area or a region of interest of the light images), the control module 281 is configured to control the light source 210 to turn on and emit a series of the excitation light pulses over a time period corresponding to the desired exposure time (each pulse causing a corresponding emission of fluorescent light from the fluorophores of the target body-part 290 for a lifetime shorter than the time period between the pulses).

Between the end of the acquisition of each light image and the starting of the acquisition of the next light image, the control module 281 is configured to maintain the excitation light unit 210 off, so as to allow the acquisition of a dark image therebetween. Preferably, the dark images are acquired using the same exposure time as their corresponding alternating light images.

The alternating light and dark images are retrieved, during their acquisition, by module 281 and stored in a light/dark image repository 283 maintained in the control unit 205 (that can be included in or separated from the mass-memory 275) or accessible by the control unit 205, in association with corresponding timestamps indicative of reference times of their acquisitions. For example, each acquired dark or light image is stored in association with at least one timestamp indicative of the start, the middle or the end of its acquisition time.

With reference now to the color imaging control module 282, it is configured to turn-on the white light source 215 that is preferably maintained in the turned-on state to constantly illuminate the field of view 104 of the imaging head 165 while the system 100 is used to inspecting the target body-part 209.

While the white light source 215 is illuminating the target body part 290, the color imaging control module 282 is further configured to control the color camera 250 to acquire, over a color acquisition channel, a sequence of color images (including for example the six color images 401-406 illustrated in FIG. 4).

For example, if the color image sensor 250*a* used in the color camera 250 is an RGB sensor, the color camera 250 is configured to combine, during image acquisition, the raw R, G, B images acquired via the R, G, B pixels of the sensor 241 so as to generate (e.g., by demosaicing) a corresponding RGB image (where each pixel is associated with three intensity values that represent how bright the pixel is in the R, G and B image planes). Furthermore, the obtained RGB image can be converted (at the camera 245 or at the control unit 205) into a YUV image, including an intensity plane (Y) along with two chroma planes (U, V) (or into any other image format associated with a color space different than RGB).

The color imaging control module 282 is configured to control the color camera 250 to acquire the color images 401-406 with an acquisition frequency greater than the acquisition frequency of the sequence of alternating dark and light images 601-603 (for example, in FIG. 4 the acquisition frequency of the color images 401-406 is twice the acquisition frequency of the images 601-603, e.g. 36 fps on average versus 18 fps on average for the color images acquisition). As such, a single dark or light image is acquired between the acquisition of two corresponding color images (for example, in FIG. 4 the dark image 601 is acquired between color images 401-402, the light image 602 is acquired between color images 403-403, and the dark image 603 is acquired between color images 405-406).

Moreover, the control modules 281, 282 preferably control the acquisition fluorescence and color channels independently of each other (although fluorescence camera 245 and the color camera 250 share the same field of view 104, these cameras can be separately controlled by the respective control modules 281, 282). As a result, sequences of color images and dark/light images are acquired over the respective channels in an asynchronous way. Thus, the timing of the color image acquisitions is generally asynchronous relative to the timing of the dark/light image acquisitions and therefore, the starting acquisition times of the dark/light images 601-603 are not aligned with the starting acquisition times of the color images (as illustrated for example in FIG. 4). Furthermore, the distance between the starting acquisition times of fluorescence and color image and/or the acquisition frequencies over the color and fluorescence channels can vary over different operations of the system 100, or even within a same operation of the system.

The color images 401-402 may be acquired with a same (or close) size and shape as the fluorescence channel images 601-603.

Moreover, it is to be noted that the exposure time to acquire a single color image is often significantly less than the exposure time used to acquire the light/dark images 601-603 (because of the larger amount of light generally available in color imaging compared to fluorescence imaging). As such, in order to improve the comparability between the color images 401-406 acquired on the color channel and the light/dark images 601-603 acquired on the fluorescence channel, the control module 282 can be optionally configured to control the color camera 250 to acquire each of two color images surrounding a given fluorescence channel image by:

- acquiring a plurality of color frames 407 (illustrated for example in FIG. 4 in relation to the first color image 401) over a time period having a duration corresponding (exactly or approximatively) to the exposure time used to acquire the given light/dark image; and
- combining (adding) together the color frames 407 to form an acquired single color image acquired over approximately or exactly the same period of exposure of the given light/dark image (it is to be noted that the image combination can be alternatively performed by the control module 282 itself or by another module of the control unit 205, upon provision of the acquired color frames 407).

The acquired color images 401-406 are retrieved by the control module 282 and stored, in association with corresponding timestamps indicative of their acquisition times (e.g., indicating the start, the middle or the end of their acquisition times), in a color images repository 284 maintained in the control unit 205.

As such, the control unit 205 stores timing information for each frame, whether a color image or a dark/light frame, indicating acquisition times of the frames relative to frames from the other channel (even if the frames are acquired asynchronously relative to each other, as illustrated for example in FIG. 4).

Acquired consecutive dark and light images can include the same (or similar) background image content caused by reflected ambient light (e.g., reflected white light emitted by the light source 215, any reflected artificial light illuminating the room where the system 100 is operated, reflected sunlight penetrating into the room, and spurious fluorescence emitted due to the white light/artificial room light/sunlight) passing through the emission filter 240 (e.g., to a non-ideal operation of the filter 240), thus reaching the sensing surface of the fluorescence image sensor 241. However, this common background image content can be spatially misaligned within the consecutive acquired dark and light images, due to movement of objects within the captured scene and/or motion of the fluorescence camera 245 relative to the captured scene.

Further configuration and functionality of the system 100 for solving this problem by performing motion-stabilized background subtraction on the fluorescence channel according to the present invention will be now described with reference to the method 300 illustrated in FIG. 3. In particular, the illustrated method 300 is disclosed in relation to the use of the system 100 during a surgical procedure (e.g., to inspect the target body-part 290 as illustrated in FIG. 2) and operates on asynchronous acquisitions of a sequence of color images and a sequence of dark/light images (that for exemplary purposes are assumed to include respectively at least the color images 401-406 and the dark/light images 601-603 illustrated in FIG. 4).

Before the surgical procedure, a healthcare operator administers to the patient a fluorescent agent (for example, Indocyanine Green, Methylene Blue or so on), which reaches the target biological body-part 109 (such as a tumor to be resected). This result may be achieved by using either a non-targeted fluorescent agent (adapted to accumulating in the target without any specific interaction therewith, such as by passive accumulation) or a targeted fluorescent agent (adapted to attaching to the target by means of a specific interaction therewith, such as achieved by incorporating a target-specific ligand into the formulation of the fluorescent agent, for example, based on chemical binding properties and/or physical structures adapted to interacting with different tissues, vascular properties, metabolic characteristics and so on). The fluorescent agent can be administered to the patient intravenously as a bolus (with a syringe); as a consequence, the fluorescent agent circulates within the vascular system of the patient until reaching the tumor and binding thereto; the remaining (unbound) fluorescent agent is instead cleared from the blood pool (according to a corresponding half-life time). After a waiting time allowing the fluorescent agent to accumulate in the tumor and to wash-out from the other body-parts of the patient (for example, from some minutes to 24-72 hours), the surgeon starts the surgical procedure by opening a cavity in the patient body to expose the target body part 290 including the administrated fluorescent substance. At this point, the operator switches on the imaging system 100 and places the imaging head 165 of the system 100 close to a region of the patient body where the surgical cavity is opened. The operator then enters a start command into the imaging system 100 (for example, using the keyboard 145).

In response to the start command, the color imaging control module 282 turns on the white light source 215 (that is preferably constantly maintained turned-on during the surgical procedure) and starts controlling the acquisition, over the color channel, of a sequence of color images (including the color images 401-406 illustrated in FIG. 4) using the color camera 250. The control module 282 stores these color images in the repository 284 (with the associated timestamps) as the sequence acquisition progresses.

Figure 3:
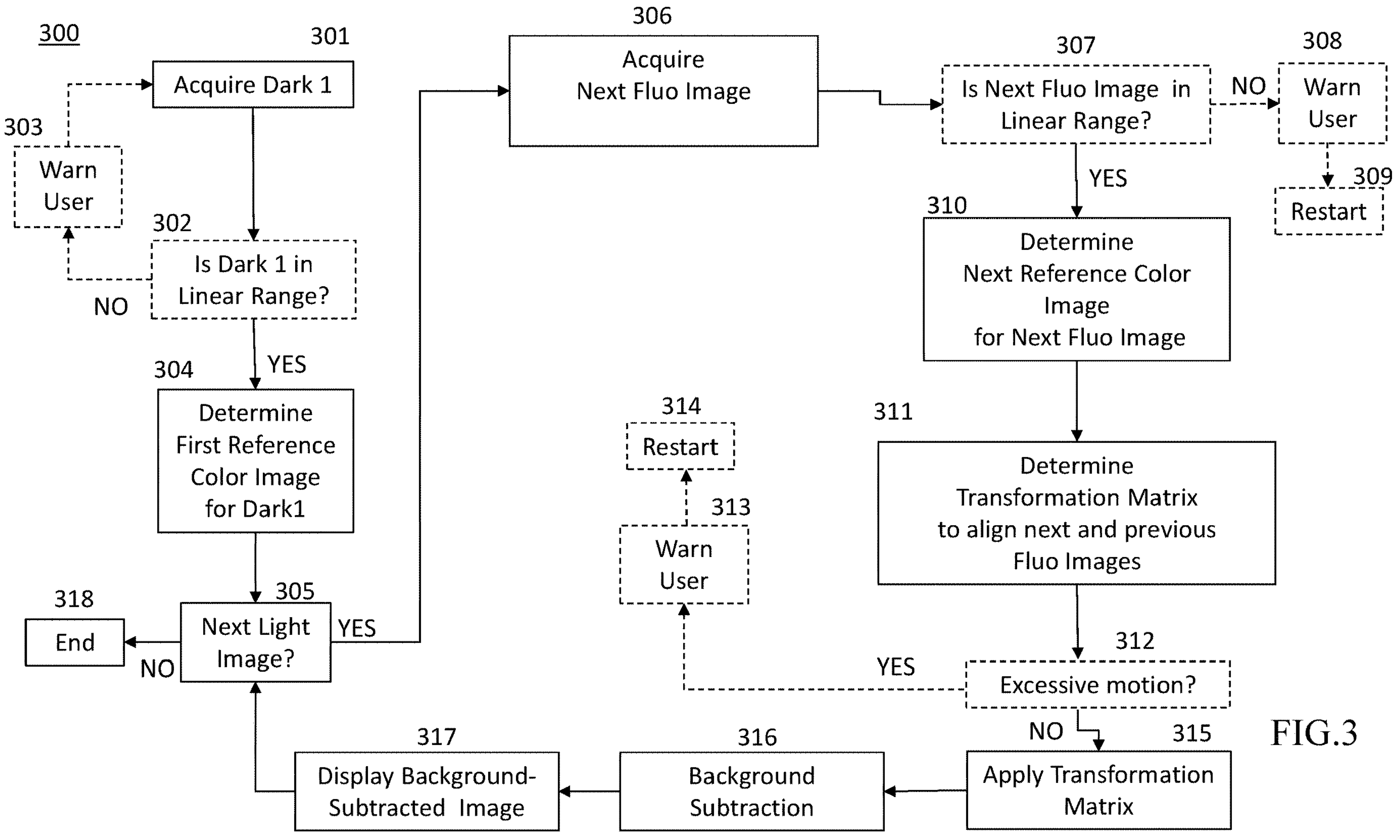
FIG. 3 illustrates a method that can be operated by the imaging acquisition system of FIG. 1 or the imaging acquisition system of FIG. 6.

While the color imaging control module 282 is controlling the acquisition of the sequence of color images over the color channel, the method 300 illustrated in FIG. 3 starts with the fluorescence imaging control module 281 controlling the fluorescence camera 245 to acquire, over the fluorescence channel, the first dark image 601 (illustrated in FIG. 4) over an exposure time $T_{exp}$ during which the excitation light source 210 is turned-off (step 301). In particular, as illustrated in FIG. 4, the first dark image 601 is acquired between the acquisitions of the two consecutive color images 401-402 over the color channel. Upon acquisition, the control module 281 stores the first dark image 601 (with the associated timestamp) within the repository 283. It is to be noted that the method 300 may equally start at step 301 with the acquisition of a first light image instead of the dark image 601, such as for example the light image 602 illustrated in FIG. 4.

Preferably, the method 300 proceeds at step 302 with the control module 281 (or any other suitable module within the control unit 205 or the fluorescence camera 245 itself) checking whether the first dark image 601 is within the linear detection range of the fluorescence image sensor 241 (i.e. whether the first dark image 601 is not overexposed).

To determine whether the first dark image 601 is within the sensor detection range, a fixed first threshold value for the pixel intensity can be set (during the sensor development) that corresponds to the highest value within the linear range of the sensor 241. A second threshold value is set, corresponding to the maximum number of pixels allowed to be above the first threshold value. Then, the number of pixels of the first dark image 601 with intensity higher than the first threshold is counted. If the counted number is higher than the second threshold, then the first dark image 201 is considered overexposed (out of range). The threshold values depend on the device hardware (for example the image sensor) and can therefore be fixed presets. The pixels checked relative to the thresholds can also be restricted to a selected region of the image (e.g., a region of interest), so that irrelevant regions of the image are ignored in the over-exposure assessment. It is to be noted that any other method can also be used for the same purpose of checking whether an acquired image is within the detection range of the sensor 241 (provided it is computationally fast enough to be performed on every new acquired image). In response to determining that the first dark image 601 is overexposed (e.g., due to some components of a strong ambient light, like an artificial light illuminating the room where the surgical operation takes place or sunshine penetrating into the room, reaching and passing through the emission filter 240), the system 100 outputs a warning (e.g., a visual and/or audible warning) for the operator, indicative of excessive ambient light (optional step 303) and then the method 300 may be restarted at step 301.

In response to determining that the first dark image is not overexposed, the method proceeds to step 304. Before disclosing the operation of step 304, it is to be noted that since the operation of step 302 is optional, the method 300 may proceed directly to step 304 after operation of step 301.

In step 304, the control module 281 (or the control module 282 or any other suitable module within the control unit 205) determines a first reference (auxiliary) color image associated with the first dark image 601 (according to the reference time of the dark image 601—indicated by the timestamp stored in association with the dark image 601). For example, it is assumed that the reference time corresponds to the start of the acquisition of the dark image 601, and that the color image 401 (illustrated in FIG. 4) is associated with the first dark image 601 as being the color image acquired before the reference time. It is to be noted that the first reference color image associated with the first dark image 601 can be alternatively selected, at step 304, as the first color image acquired after the reference time and/or the reference time can correspond to other times during the acquisition of the first dark image 601, e.g., the middle time or the end time of the acquisition of the first dark image 601.

The method 300 proceeds with the imaging control module 281 (or any other module within the control unit 205) determining whether there is a next fluorescence channel image (namely a light image) to be acquired after the first dark image 601 over the fluorescence channel (step 305).

In response to determining that a first light image 602 is to be acquired over the fluorescence channel after the first dark image 601, the method 300 proceeds with the fluorescence imaging control module 281 controlling the excitation light source 210 to turn-on and the fluorescence camera 245 to acquire, over the fluorescence channel, the first light image 602 over an exposure time $T_{exp}$ during which the excitation light source 210 is used to cause the fluorescent substance in the target-body part 290 to emit fluorescent light (step 306). In particular, as illustrated in FIG. 4, the first light image 602 is acquired between the acquisitions of the two consecutive color images 402-403 over the color channel. Upon acquisition, the control module 281 stores the first light image 602 (with the associated timestamp) within the repository 283.

Preferably, the method 300 proceeds with the control module 281 (or any other suitable module within the control unit 205 or the fluorescence camera 245) checking whether the first light image 602 is within the linear detection range of the fluorescence image sensor 241 (optional step 307), in a way similar to the previously disclosed optional step 302.

In response to determining that the first light image 602 is overexposed, at step 308 the system 100 outputs a warning for the operator, in a way similar to the previously disclosed optional step 303. The method 300 may then be restarted (optional step 309, starting again from step 301). Alternatively, the method 300 may re-execute step 306 until a first light image which is not overexposed is acquired.

The method 300 then proceeds at step 310 with the control module 281 (or the control module 282 or any other suitable module within the control unit 205) determining a second reference color image associated with the first light image 602 (according to the reference time of the light image 602—indicated by the timestamp stored in association with the light image 602). For example, the color image 403 (illustrated in FIG. 4) is associated with the first light image 602 (in a way similar to the association of the first reference color image 401 with the first dark image 601 at step 304).

At this stage, the method 300 proceeds with the color imaging control module 282 (or the fluorescence imaging control module 281 or any other module within the control unit 205) determining at step 311 a transformation matrix suitable for aligning the first dark and light images 601, 602, based on a relative alignment of the associated first and second reference color images 401, 403.

It is to be noted that the matrix transformation calculated at step 311 can accurately estimate the motion occurring between the first dark and light images 601, 602 based on the information provided by the reference color images 401, 403, at least because:

- the color camera 240 can have a significantly higher resolution than the fluorescence camera 245 (therefore the transformation matrix can be effectively extrapolated); and
- the color images are stable in terms of pixel-intensity.

In more detail, according to some embodiments, a first interpolation factor $\varphi_1$ is calculated using the stored timestamps indicative of the acquisition times of the two color images 401-402 and the reference time of the first dark image 601 (the interpolation factor $\varphi_1$ being indicative of the acquisition times of the color images 401-402 relative to the reference time of the first dark image 601). For example, considering $t_{C1}$, $t_{C2}$ and $t_{D1}$ the stored timestamps of the two color images 401, 402 and the first dark image 601, respectively, the interpolation factor $\varphi_1$ can be computed as the following fraction:

$$\varphi_1 = (t_{D1} - t_{c1})/(t_{c2} - t_{c1}), \text{ with}$$

$$\varphi_1 \in [0, 1].$$

Two exemplary techniques to obtain a first interpolated transformation matrix suitable for aligning the first reference color image 401 to the first dark image 601, using the interpolation factor $\varphi_1$, are now disclosed. Both of these exemplary techniques are based on calculating a transformation matrix representing a transformation estimating an underlying motion occurring between the acquisitions of the color images 401, 402 (causing a proportional spatial (pixel-wise) misalignment between the color images 401, 402). In particular, reference will be made for example to Affine Warping and Perspective Warping for extracting the transformation matrix. These transformation algorithms are generally used for estimating and correcting camera motion in video-stabilization techniques. In particular, Affine Warping and Perspective Warping are implemented and included in the OpenCV library (https://docs.opencv.org/3.4/(also disclosed in Bradski, The OpenCV Library, Dr. Dobb's Journal of Software Tools). Moreover, Affine Warping and Perspective Warping are disclosed for example in Shi, J., Good features to track, in 1994 Proceedings of IEEE conference on computer vision and pattern recognition. However, it is to be appreciated that other alternative known transformation algorithms applied in video-stabilization (or other imaging applications) can be used to extract motion transformation matrices associated with the color images 401, 402.

According to the first exemplary technique, a transformation matrix for the color images 401, 402 is calculated using Affine Warping. In particular, at least three features (landmarks) are extracted from one of the images 401, 402 and tracked in the other image in order to estimate an affine transformation matrix expressing the following three basic components of movement between the color images 401, 402: rotations (linear transformation), translations (vector addition) and scale operations (linear transformation). The affine transformation matrix can be a 2×3 matrix with the following structure:

$$\begin{bmatrix} \cos(\theta)\cdot s & -\sin(\theta)\cdot s & t_x \\ \sin(\theta)\cdot s & \cos(\theta)\cdot s & t_y \end{bmatrix}$$

where θ is the rotation angle, s is the scaling factor and $t_x$, $t_y$ are translations along the x, y axes respectively.

After the affine transformation matrix has been computed, the affine transformation matrix is decomposed into its dimensional motion components, including computing the scaling factor s and the rotation angle θ as follows:

$$s = \left\| \begin{bmatrix} \cos(\theta)\cdot s \\ \sin(\theta)\cdot s \end{bmatrix} \right\|^2$$

$$\theta = \arctan\left(\frac{\sin(\theta)\cdot s}{\cos(\theta)\cdot s}\right)$$

The calculated interpolation factor $\varphi_1$ between the color images 401, 402 is then used to obtain interpolated versions of the dimensional components, as follows:

$$\tilde{t_x} = t_x \cdot \varphi$$

$$\tilde{t_y} = t_y \cdot \varphi$$

$$\tilde{s} = s + (1 - s)\cdot \varphi$$

$$\tilde{\theta} = \theta \cdot \varphi$$

A new, interpolated, affine transformation matrix is then reassembled from the interpolated components:

$$\begin{bmatrix} \cos(\tilde{\theta})\cdot \tilde{s} & -\sin(\tilde{\theta})\cdot \tilde{s} & \tilde{t_x} \\ \sin(\tilde{\theta})\cdot \tilde{s} & \cos(\tilde{\theta})\cdot \tilde{s} & \tilde{t_y} \end{bmatrix}$$

According to the second exemplary technique, a transformation matrix for the color images 401, 402 is calculated using Affine Warping or Perspective Warping (or any other motion transformation algorithm) and then directly interpolated to obtain an interpolated (fractional) transformation matrix using fractional matrix power algorithm (a technique disclosed for example in Nicholas J. Higham and Lijing lin, A Schur-Pade Algorithm for Fractional Powers of a Matrix, SIAM Journal on Matrix Analysis and Applications, 2011). In this regard, since fractional matrix power is applicable only on square matrices, in case of using Affine Warping to determine an affine transformation matrix, a last row [0, 0, 1] is added for example to the 2×3 affine transformation matrix (to obtain a 3×3 matrix).

Indicating as T the transformation matrix on which fractional matrix power is going to be applied and assuming that this matrix is diagonalizable, then there exists an orthogonal matrix P and a diagonal matrix D such that:

$$T = PDP^{-1}$$

The entries of D are the eigenvalues of T and P contains the respective eigenvectors.

Using the calculated interpolation factor φ between the color images 401, 402, the ${\varphi_1}^{th}$ power of the matrix T is determined as:

$$T^{\varphi} = PD^{\varphi}P^{-1}$$

(wherein if $\varphi_1=0$, $T^{\varphi}$ corresponds to the identity matrix, and if $\varphi_1=1$, $T^{\varphi}$ corresponds to T). Based on the above disclosed principles, a second interpolation factor $\varphi_2$ is calculated using the stored timestamps indicative of the acquisition times of the two color images 403-404 and the reference time of the first light image 602, and a second interpolated transformation matrix suitable for aligning the second reference color image 403 to the first light image 602 is determined (using the interpolation factor $\varphi_2$).

According to some embodiments, a transformation matrix representing a transformation estimating any underlying motion occurring between the acquisitions of the first dark image 601 and the first light image 602 (causing a corresponding spatial (pixel-wise) misalignment between the first dark and light images 601, 602) is then determined at step 311 as a function of the first and second reference color images 401, 403, and the calculated first and second interpolated transformation matrices.

According to some alternative embodiments, the calculated first and second interpolated transformation matrixes are applied respectively to the first and second reference color images 401 and 403 to obtain a first virtual color image 408 approximatively aligned to the first dark image 601, and a second virtual color image 409 approximatively aligned to the first light image 602 (as illustrated for example in FIG.

4). The first virtual color image 408 has a field of view (framing view) substantially overlapping the field of view of the first dark image 601, and the second virtual color image 409 has a field of view (framing view) substantially overlapping the field of view of the first light image 602. In practice, the first and second virtual color images 408, 409 approximate the field of view (imaged content and related position within the frame) that a color image would have had if acquired at the reference times of the respective first dark and light images 601, 602. The obtained first and second virtual color images 408, 409 can be stored within the color images repository 284 (or a repository dedicated in the central unit 205 for storing virtual color images) in association with respective intermediate timestamps between the timestamps of the color images 401-402 and 403-404.

At this stage, at step 311 a transformation matrix is determined to align the first and second virtual color images 408, 409. For example, affine Warping and Perspective Warping, previously disclosed, can be used to determine this transformation matrix (or any other transformation algorithms applied in video-stabilization or any other imaging application). Since the first and second virtual color images 408, 409 are approximatively aligned to the first dark and light images 601, 602, respectively, this transformation matrix also represents a transformation estimating any underlying motion occurring between the acquisitions of the first dark image 601 and the first light image 602.

According to some other alternative embodiments, the calculated first and second interpolated transformation matrixes are applied respectively to align the first dark image 601 to the first reference color image 401, and the first light image 602 to the second reference color image 403. At step 311 a transformation matrix is then determined, suitable for aligning the first and second reference color images 401, 403 (and, therefore, suitable for aligning the first dark and light images 601, 602).

With reference back to the method step 304, according to some alternative embodiments, the closest in time of the color images 401, 402 to the reference time of the first dark image 601 is determined as the first reference color image assigned to the dark image 601. In practice, if the calculated interpolation factor 1 is lower or equal than 0.5, then the first color image 401 is assigned to the dark image 601 as the first reference color image. Otherwise, the second image 402 is assigned to the dark image 601 as the first reference color image. Similarly, with reference back to method step 310, the closest in time of the color images 403, 404 to the reference time of the first light image 602 is determined as the second reference color image assigned to the light image 602.

At this stage, at step 311 a transformation matrix is determined to align the selected first and second reference color images. Based on the assumption that the acquisition times of the selected reference color images are close enough to the reference times of the associated first dark and light images 601, 602, this transformation matrix also represents a transformation estimating any underlying motion occurring between the acquisitions of the first dark image 601 and the first light image 602.

Preferably, after step 311, according to optional step 312 the method 300 comprises determining whether the underlying motion estimated by the determined transformation matrix is excessive (e.g., above a certain threshold). In response to determining an excessive estimated motion, the system 100 outputs a warning for the operator indicative of excessive motion (either of the objects within the illuminated scene or of the imaging head 165 including the fluorescence and color cameras 245, 250). Then, the method 300 may be restarted from step 301 (or alternatively may return back to step 305).

In response to determining that there is not excessive motion, the method proceeds to step 315. Before disclosing the operation of step 315, it is to be noted that since the operation of step 312 is optional, the method 300 may proceed directly to step 315 after operation of step 311.

At this stage, the fluorescence imaging control module 281 (or the color imaging control module 282 or any other module within the control unit 205) applies to the first dark image 601 the matrix transformation determined at step 311 in order to correct the estimated motion by spatially (pixel-wise) aligning the first dark image 601 to the light image 602.

In this way, any common background image content within the first dark and light images 601, 602 (due to ambient light) and originally misaligned between the first dark and light images 601, 602 (due to motion) can be advantageously (at least approximatively) realigned by applying the transformation matrix to the first dark image 601 (before performing background subtraction).

The fluorescence imaging control module 281 (or the color imaging control module 282 or any other module within the control unit 205) then proceeds at step 316 to perform a motion-stabilized background subtraction by subtracting (pixel-wise subtraction) the corrected first dark image 601 from the first light image 602 (with improved background reduction by comparison to performing a direct subtraction between the unmodified first dark and light images 601, 602, due to the applied alignment of the first dark image 601 to the first light image 602).

The background-subtracted image fluoresce image so obtained is stored in the image repository 283 (or a repository dedicated in or accessible by the central unit 205 for storing background subtracted images), possibly with an associated timestamp.

Moreover, at step 317 the background-subtracted image is displayed, generally overlaid on a color image (e.g., to form a combined image), as a part of a displayed real-time video stream (representing the fluorescent target body-part 290 being contextualized on the surrounding anatomical parts of the patient body). According to the above disclosed embodiments where the virtual color images 408, 409 are generated, the color image on which the background-subtracted image is superimposed can be the virtual color image 409 assigned to the light image 602 used to generate the background-subtracted image (or it can be one of color images 403, 404).

In the embodiment, background-subtracted images are generated after acquiring each image, whether dark or light, on the fluorescence channel, although it will be appreciated that in other embodiments a background-subtracted image might only be generated for each new dark/light image pair acquired on the fluorescence channel. As such, in the embodiment, the method 300 returns back to step 305 and, in response to determining that there is a next image (namely a new dark image) to be acquired over the fluorescence channel, at step 306 the second dark image 603 (illustrated in FIG. 4) is acquired over an exposure time $T_{exp}$ during which the excitation light source 210 is not used to cause the fluorescent substance present in the target-body part 290 to emit fluorescent light.

In response to determining that the second dark image 603 is not overexposed, step 310 is performed to determine a third reference color image 405 associated with the second dark image 603 based on the reference time of the second dark image 603 indicated by the timestamp stored in association with the dark image 603 (according to the same principles previously disclosed for the association of the first and second reference color images 401, 403 with the first dark and light images 601, 602). The obtained third virtual color image 410 is stored in association with an intermediate timestamp between the timestamps of the color images 405, 406.

At this stage, at step 311 the method 300 can proceed to determine a matrix transformation estimating any underlying motion occurring between the first light image 602 and the second dark image 603 (according to the same principles previously disclosed for the determination of the transformation matrix to align the first dark image 601 and the first light image 602).

According to optional step 312, in response to determining that there is no excessive motion, the method 300 proceeds by applying the determined matrix transformation to the first light image 602 (step 315), in order to correct the motion between the first light image 602 and the second dark image 603.

At step 316 a motion-stabilized background subtraction is then operated by subtracting the second dark image 603 from the corrected first light image 602.

At step 317 the background-subtracted image fluoresce image so obtained is then stored and displayed, overlaid on an associated color image, as a part of the displayed real-time video stream. Again, according to embodiments where a virtual color image 410 is obtained and assigned to the second dark image 603 (as illustrated for example in FIG. 4), the associated color image can be the virtual color image 410 (or one of the color images 405, 406).

The method 300 then returns again back to step 305 and iteratively operates steps 306-317 in relation to new acquired alternating light/dark images, resulting in new background-subtracted fluorescence images being generated with motion correction and displayed in sequence (overlaid on respective associated color images) as part of the displayed real-time video stream. In particular, at each iteration a new reference color image is assigned to the newly acquired fluorescence channel image (at step 310), a transformation matrix is determined (at step 311) based on a relative alignment between the new reference color image and the reference color image previously assigned to the previous fluorescence channel image, and the transformation matrix is applied (at step 315) to the previous fluorescence channel image. If the newly acquired fluorescence channel image is a light image, then the transformed previous dark image is subtracted (at step 316) from the newly acquired light image; if the newly acquired fluorescence channel image is a dark image, then the newly acquired dark image is subtracted (at step 316) from the transformed light image.

The method 300 continues in this way until at step 305 there is determined that there are no further images to be acquired over the fluorescence channel (e.g., because the surgical operation has terminated and the operator has provided a stop command). At this stage, at step 318 the method 300 ends.

Whereas the above disclosed operation of the system 100 for performing motion stabilized background subtraction applies to an asynchronous control of the color and fluorescence channels, an operation of the system 100 for performing motion stabilized background subtraction is now disclosed in relation to an alternative way of controlling the channels, whereby the imaging control modules 281 and 282 maintain synchronization between the acquisition of the alternating dark/light images 601-603 and the acquisition of corresponding color images 401-406, so that the reference time of each fluorescence channel image (either a dark or light image) is aligned with the acquisition time of a corresponding color image. For example, in FIG. 5, the dark image 601 is acquired between the acquisitions of the color images 401 and 402, with the starting time of the acquisition of the dark image 601 substantially aligned to the starting time of the acquisition of the corresponding color image 401; the light image 602 is acquired between the acquisitions of the color images 403 and 404, with the starting time of the acquisition of the light image 602 substantially aligned to the starting time of the acquisition of the corresponding color image 403; and the dark image 603 is acquired between the acquisitions of the color images 405 and 406, with the starting time of the acquisition of the dark image 603 substantially aligned to the starting time of the acquisition of the corresponding color image 405.

In order to perform motion correction background subtraction when the sequences of color and fluorescence channel images are synchronously acquired, the system 100 can be configured to perform the same method 300 previously disclosed, but with the difference that the determination (at steps 304, 310) of a reference color image for a given acquired fluorescence channel image (either dark or light image) can be simply performed by selecting the color image whose acquisition is temporally aligned with the reference time of the given fluorescence channel image (based on the appreciation that this color image has the framing view more closely overlapping to the framing view of the given fluorescence channel image). For example, with reference to FIG. 5, the operation of the method 300 so modified will assign color image 401, color image 403 and color image 405 as reference color images for dark image 601, light image 602, and dark image 603, respectively.

Figure 6:
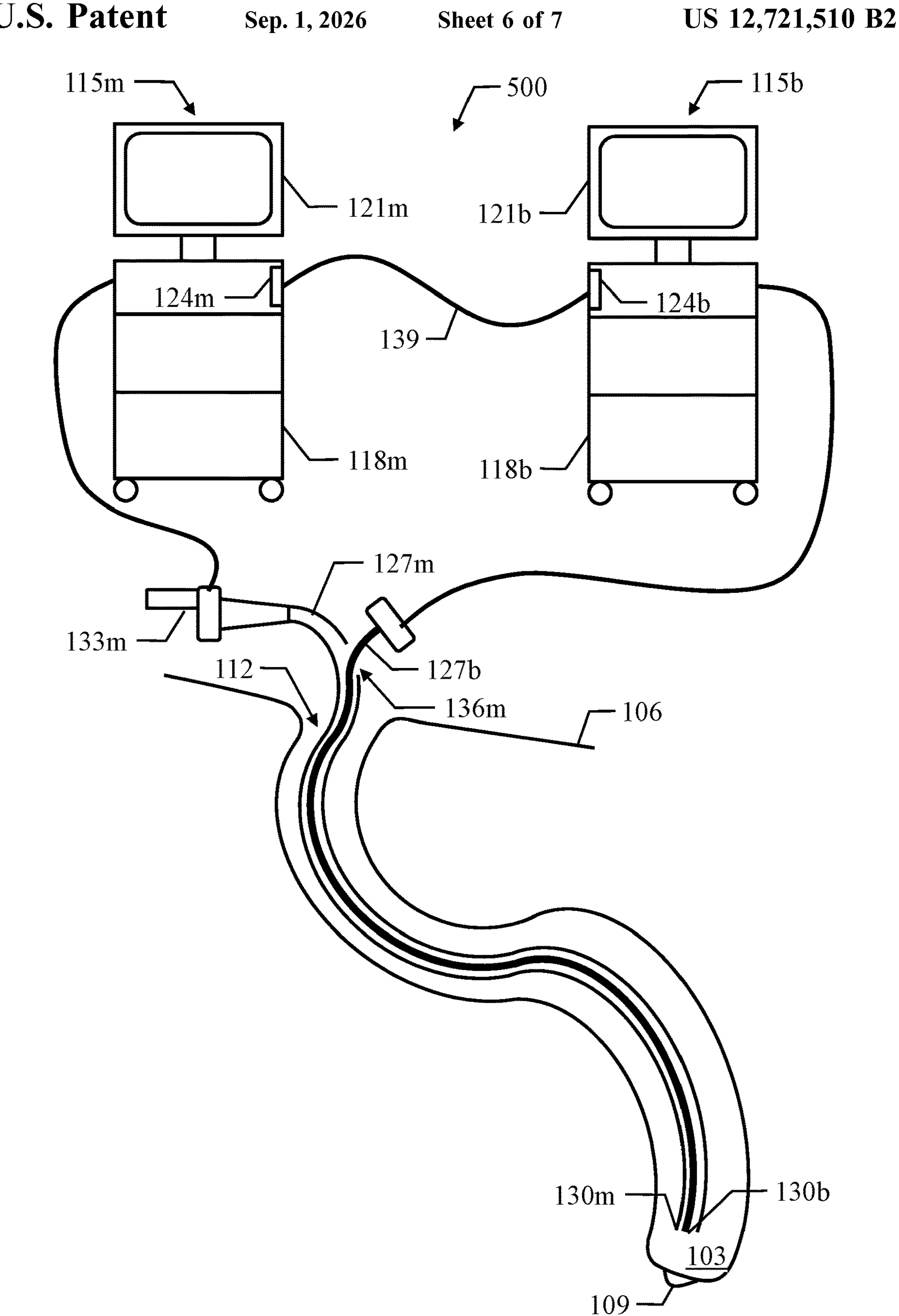
FIG. 6 illustrates an imaging acquisition system for endoscopy, configured to operate motion-stabilized fluorescence background subtraction according to an embodiment of the present invention.

With reference now to FIG. 6, there is illustrated an imaging system for endoscopy, or simply endoscopic system, 500 according to an embodiment of the present disclosure, that is also configured to operate motion-stabilized fluorescence background subtraction according to an embodiment of the present invention.

In particular, the endoscopic system 500 is used in a medical procedure for imaging an internal body-part 103 of a patient 106 delimiting a body cavity (which is not normally visible). The body cavity is accessible through an opening 112, being either a natural orifice or a small incision in the skin of the patient 106. The body-part 103 comprises a target body region of interest 109 of a medical procedure (for example, a lesion, such as a tumor) including a fluorescent substance (for example, a fluorescent agent adapted to accumulating in tumors that has been previously administered to the patient 106).

For example, in diagnostic applications the endoscopic system 500 allows discovering/monitoring lesions; in (minimally invasive) surgical applications the endoscopic system 500 allows identifying lesions to be resected, and in therapeutic applications the endoscopic system 500 allows delineating lesions to be treated. Examples of these medical procedures are gastroscopy, colonoscopy, esophagoscopy and so on for the diagnostic applications; they are arthroscopy, laparoscopy, thoracoscopy and so on for the surgical applications; and they are cauterization, dilatation, stenting and so on for the therapeutic applications.

The endoscopic system 500 is used to apply a fluorescence (endoscopic) technique for displaying the fluorescent substance in the region of interest 109 within the body cavity in combination with a standard (endoscopic) technique (for displaying what is visible to human eye in the body cavity, when illuminated). For this purpose, the endoscopic system

500 is composed of two endoscopic units, i.e., a main endoscopic unit, or simply “motherscope”, 115*m* combined with an auxiliary endoscopic unit, or simply “babyscope”, 115*b*.

The motherscope 115*m* comprises the following components. A central unit of the motherscope 115*m* is used to manage its operation. For example, the central unit is implemented as a trolley 118*m*. A monitor 121*m* (for example, mounted on top of the trolley 118*m*) is used to display images of the body-part 103 during the medical procedure. A video interface 124*m* (for example, a Serial Digital Interface (SDI) port on the back of the trolley 118*m*) is used to exchange video information with the outside. A probe 127*m* (coupled with the trolley 118*m*, for example, via a cable) is used to operate on the patient 106. For example, the probe 127*m* is implemented as an elongated shaft for insertion into the cavity of the body-part 103; the shaft of the probe 127*m* may be rigid or preferably flexible to allow its sliding through the cavity of the body-part 103 (even when the cavity has a curved path). A distal end, or tip, 130*m* of the probe 127*m* is used to reach the region of interest 109, for illuminating and acquiring color images (as described in more detail in the following).

A proximal end of the probe 127*m* (outside the cavity 103) is provided with a handle 133*m* for driving the tip 130*m* (via control cables, not shown in the figure). The probe 127*m* has one or more working channels (accessible through corresponding one or more working ports close to its proximal end), only one being shown in the FIG. 6 (denoted with the reference 136*m*). The working channels allow inserting different tools to be used during the medical procedure (for example, snares, forceps, knife, clip applier and so on); a dedicated working channel may also be connected to a fluid injector/extractor (not shown in the figure) for cleaning the tip 130*m* and the cavity of the body-part 103 during the medical procedure.

The babyscope 115*b* comprises the following components. Similarly to the motherscope 115*m*, the babyscope 115*b* comprises a central unit used to manage its operation. For example, the central unit is implemented as a trolley 118*b*. A monitor 121*b* (for example, mounted on top of the trolley 118*b*) is used to display (further) images of the cavity of the body-part 103 during the medical procedure. A video interface 124*b* is used to exchange video information with the outside. A probe 127*b* (coupled with the trolley 118*b*, for example, via a cable) is used to operate on the patient 106. For example, the probe is implemented as a (preferably flexible) elongated shaft. A distal end, or tip, 130*b* of the probe 127*b* is used to reach the same region of interest of the medical procedure within the cavity of the body-part 103 for illuminating and acquiring fluorescence and color images thereof (as described in more detail in the following). In a specific implementation, the probe 127*b* is thinner than the probe 127*m*. The probe 127*b* is inserted into the working channel 136*m*, until its tip 130*b* reaches the tip 130*m* of the probe 127*m* (without impairing a maneuverability of the latter due to its size and flexibility).

Figure 7:
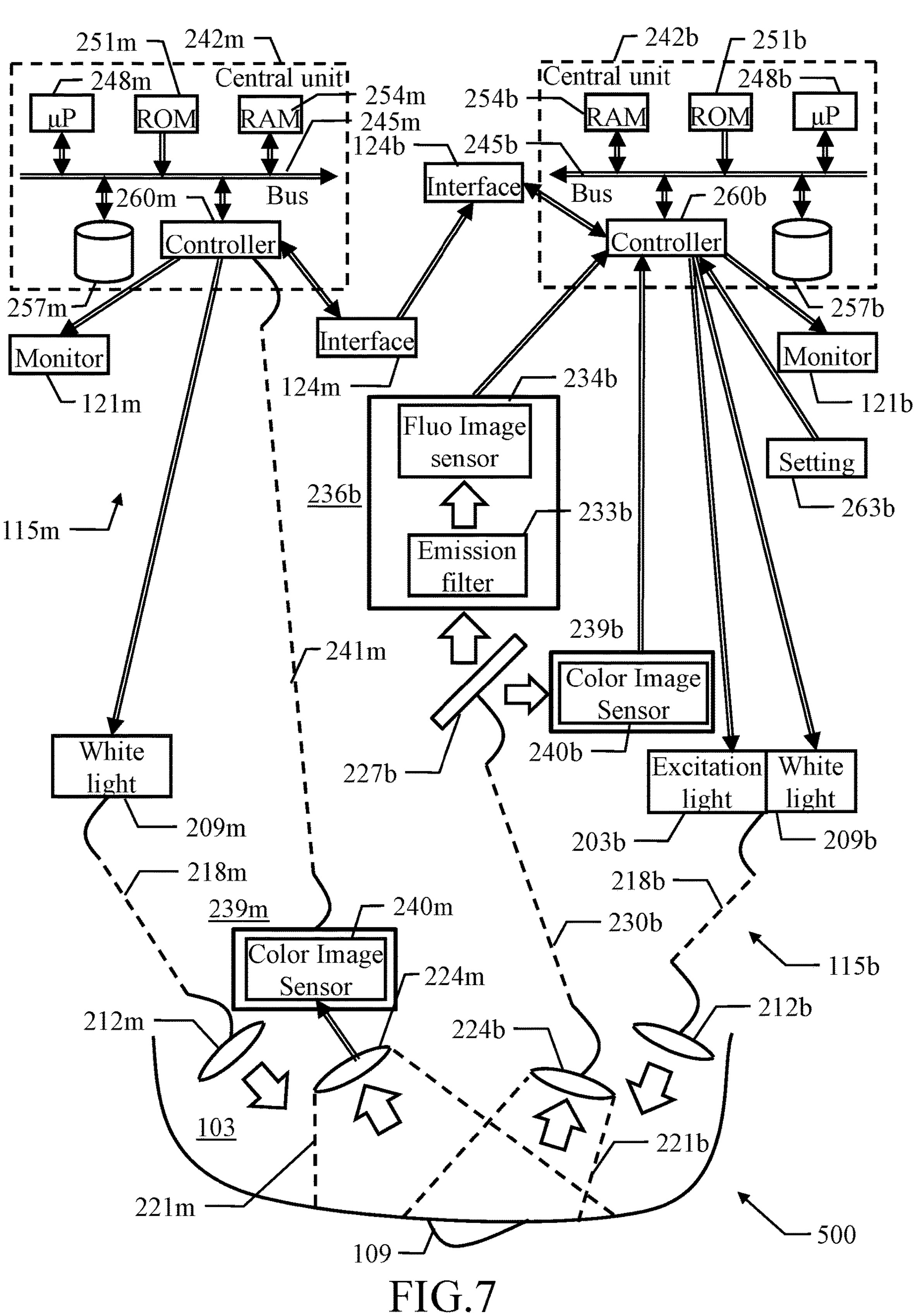
FIG. 7 illustrates a block diagram of the imaging acquisition system of FIG. 6.

With reference now to the functional block diagram of the endoscopic system 500 illustrated in FIG. 7, the motherscope 115*m* is described in more detail. In particular, the motherscope 115*m* comprises at least an image acquisition unit, for acquiring images of the region of interest 109 of the body-part 103 within a corresponding field of view 221*m*, and an illumination unit that is used to illuminate the region of interest 109.

Starting from the illumination unit, it comprises a white light source 209*m* (for example, a LED, halogen, or Xenon lamp, e.g., within the trolley 118*m*) configured to emit white light that is transmitted, by an incoherent bundle of optical fibers 218*m* (along the probe), to delivery optics 212*m*. The delivery optics 212*m* (at the tip of the probe of the motherscope 115*m*) is configured to deliver the received white light to the body part 103 (including the region of interest 109) within the field of view 221*m*.

Moving to the image acquisition unit of the motherscope 115*m*, it comprises collection optics 224*m* configured to collect visible light that is reflected by any object present in the field of view 221*m* illuminated by the white light. The image acquisition unit further comprises a color camera 239*m* including at least a color image sensor 240*m* (for example, of CCD type) suitable for detecting the collected visible light and generating in response color images representing what is visible to human eye within the illuminated field of view 221*m*.

In a video-scope configuration, the color camera 239*m* is arranged at the tip of the probe; in this case, a digital connection 241*m* transmits the acquired color images to the trolley 115*m* (alternatively, the color camera 239*m* can be arranged inside the trolley 115 and a coherent bundle of optical fibers can be used to transmit the visible light from the collection optics 224*m* to the color camera 239*m*).

With reference now to the babyscope 115*b* schematically illustrated in FIG. 7, it comprises at least an image acquisition unit, for acquiring images of the region of interest 109 of the body-part 103 within a corresponding field of view 221*b*, and an illumination unit that is used to illuminate the region of interest 109. Generally, the field of view 221*b* of the babyscope 115*b* and the field of view 221*m* of the motherscope 115*m* are different. For example, the field of view 221*b* is smaller than the field of view 221*m* and overlaps (at in least in part) the field of view 221*m* (so as both the fields of view 221*b*, 221*m* include the target body region of interest 109, as in the example shown in the FIG. 7).

Starting from the illumination unit, it includes a NIR excitation light source 203*b* (for example a laser source, or LEDs, e.g., inside the trolley of the babyscope 115*b*) configured to emit excitation light. The excitation light has wavelength and energy suitable for exciting the fluorophores of the fluorescent substance present in the target body region of interest 109, so as to cause the emission of fluorescent light within a corresponding fluorescence emission NIR spectrum.

The illumination unit of the babyscope 115*b* further includes a white light source 209*b* (e.g., inside the trolley 118*b*, for example, a LED, halogen, or Xenon lamp, e.g. inside the trolley 118*b*) configured to emit white light.

An incoherent bundle of optical fibers 218*b* (along the probe) is configured to transmit the emitted excitation light and the emitted white light (mixed together, if emitted at the same time) to delivery optics 212*b* (at the tip of the probe, not shown in FIG. 7). The delivery optics 212*b* is configured to deliver the received excitation light and the white light to the body-part 103 within the field of view 221*b* of the image acquisition system, so as to illuminate the region of interest 109. Alternatively, two separate pieces of delivery optics, with corresponding incoherent bundles of optical fibers, can be used to independently deliver the excitation light and the white light from the respective light sources 203*b*, 209*b* to the body-part 103 within the field of view 221*b*.

Moving to the image acquisition unit of the babyscope 115, it comprises collection optics 224*b* configured to collect light present within the field of view 221*b*. The collected light within the field of view 221*b* can comprise: fluorescent light that is emitted by the fluorophores present in the target region of interest 109 (in response to absorbing the excitation light provided by the light source 203*b*); any spurious fluorescent light that can be emitted by fluorophores other than the fluorophores of the target fluorescent agent, such as endogenous fluorophores present within the inspected body region of interest 109 (in response to absorbing some components of the white light provided by the light source 215 or the white light provided by the light source 209*m* of the motherscope 115*m*); and excitation light reflected by objects present in the field of view 221*b*. Moreover, the collected light can comprise visible light that is reflected by any object present in the field of view 221*b*, illuminated by the white light emitted by the light source 209*b* or by the light source 209*m* of the motherscope 115*m*.

The image acquisition unit further comprises a coherent bundle of optical fibers 230*b* (along the probe) configured to transmit the collected light from the collection optics 224*b* to a beam-splitter 227*b*. Similarly to the beam-splitter 235 previously disclosed for the system 100 illustrated in FIG. 2, the beam-splitter 227*b* (e.g., a dichroic mirror) is configured to split the collected light into two channels, namely a first channel of collected light within a NIR spectrum (including the fluorescence emission spectrum) and a second channel of collected light within the visible light spectrum.

The image acquisition unit further comprises a fluorescence camera 236*b* including at least a fluorescence image sensor 234*b* and an associated emission filter 233*b*. Similarly to the emission filter 240 previously disclosed for the system 100 illustrated in FIG. 2, the filter 233*b* is a passband filter having a fluorescence detection passband corresponding to the fluorescence emission spectrum of the fluorescent substance present in the target body region of interest 109, while preventing the passage therethrough (in ideal operation) of any components of the excitation light reflected by objects within the field of view 221*b* or any reflected ambient light different than the fluorescent light and the excitation light (including e.g., small portions of the white light emitted by the white light source 209*b* or the white light source 209*m* of the motherscope 115*m*, that can fall within the NIR spectrum or have been wrongly deviated towards the filter 233*b* due to not-ideal operation of the beam-splitter 227*b*).

Similarly to the image sensor 241 of the previously disclosed system 100 of FIG. 2, the image sensor 234*b* can be any high-sensitive sensor for low-light imaging in NIR.

With reference back to the second channel of the beam-splitter 227*b*, the image acquisition unit of the babyscope 115*b* further includes a color camera 239*b*. Similarly to the color camera 250 of the previously disclosed system 100, the color camera 239*b* includes an image sensor 240*b* (e.g., of the CCD or CMOS type) capable of separately detecting the intensity of separate color components of incoming reflected light (for example with an RGB filer or other CFA).

With reference still to FIG. 7, a central unit 242*b* and a central unit 242*m* are used to control operation of the babyscope 115*b* and of the motherscope 115*m*, respectively. Each central unit 242*b*, 242*m* comprises several units that are connected to each other through a bus structure 245*b*, 245*m*. In particular, each central unit 242*b*, 242*m* comprises at least one microprocessor (uP) 248*b*, 248*m* configured to provide a logic capability of the central unit 242*b*, 242*m*. A ROM 251*b*, 251*m* stores basic code for a bootstrap of the central unit 242*b*, 242*m*, and a RAM 254*b*, 254*m* is used as a working memory by the microprocessor 248*b*, 248*m*. The central unit 242*b*, 242*m* is provided with a mass-memory 257*b*, 257*m* for storing programs and data. Moreover, each central unit 242*b*, 242*m* comprises a number of controllers 260*b*, 260*m* for peripherals (I/O units). In particular, the controllers 260*m* of the motherscope 115*m* include at least a color imaging control module configured to control the operation of the white light source 209*m* and the color camera 239*m* to acquire a sequence of color images that are stored in a color images repository maintained in the central unit 242*m* (e.g. a repository within the mass-memory 275*m* or any other dedicated repository within or accessible by the central unit 242*m*).

The controllers 260*b* of the babyscope 115*b* include at least a fluorescence imaging control module and a color imaging control module which are configured to control the operation of the excitation light source 203*b*, the fluorescence camera 236*b*, the white light source 209*b*, and the color camera 239*b* of the babyscope 115*b* to acquire and store sequences of color and alternated dark/light images, similarly to previously disclosed acquisition and storing of color and alternated dark/light images as per the configuration of the control modules 281-282 of the imaging head 165 of the system 100.

In particular, similarly to the fluorescence imaging control module 281 of the imaging head 165 of the system 100, the fluorescence imaging control module of the babyscope 115*b* is configured to:

- coordinate the operation of the fluorescence camera 236*b* and the turning on/off of the excitation light source 203*b* so as to acquire, over a fluorescence acquisition channel, light fluorescence images (acquired using the excitation light source 203*b*) alternating with the same shape and size dark images (acquired without using the excitation light source 203*b*) (as for example the fluorescence channel images 601-603 illustrated in FIG. 4); and
- store the acquired alternated dark/light images 601-603 in a respective fluorescence channel images repository (e.g. a repository within the mass-memory 275*b* or any other dedicated repositories within or accessible by the central unit 242*b*), in association with corresponding timestamps indicative of their acquisition times.

In order to acquire the light images during an appropriate exposure time, the fluorescence imaging control module is configured to control the light source 203*b* to turn on and emit a series of the excitation light pulses over a time period corresponding to the desired exposure time. In order to acquire the dark images, the fluorescence imaging control module is configured to maintain the excitation light source 203*b* off between the end of the acquisition of each light image and the starting of the acquisition of the next light image.

Similarly to the color imaging control module 282 of the imaging head 165 of the system 100, the color imaging control module of the babyscope 115*b* is configured to:

- turn-on the white light source 209*b* that is preferably maintained in the turned-on state to constantly illuminate the field of view 221*b* of the babyscope 115*b* (while the babyscope 115*b* is positioned close to and used to inspect the target body region of interest 109); and
- while the white light source 209*b* is illuminating the target body region of interest 109, control the color camera 239*b* to acquire, over a color acquisition channel, a sequence of color images (including for example the color images 401-406 illustrated in FIG. 4), with an acquisition frequency greater than the acquisition frequency of the sequence of alternating dark/light images 601-603).

Moreover, similarly to the imaging control modules 281, 282 of the imaging head 165 of the system 100, the fluorescence and color imaging control modules of the babyscope 115*b* preferably control the acquisition fluorescence and color channels independently of each other. As a result, sequences of color images and fluorescence channel images are acquired over the respective channels in an asynchronous way (as illustrated for example in FIG. 4).

The color images 401-406 may be acquired with a same (or close) size and shape as the fluorescence channel images 601-603 (and, optionally, each color image 601-603 can be acquired over an acquisition time corresponding to the exposure time $T_{exp}$ of the corresponding alternate dark/light images 601, 602, 603, by combining a plurality of color images sequentially acquired with lower exposure times, as for instance illustrated in FIG. 4).

The color images 401 are stored by the color imaging control module in a respective color images repository (e.g. a repository within the mass-memory 275*b* or any other dedicated repositories within or accessible by the central unit 242*b*), in association with corresponding timestamps indicative of their acquisition times.

Acquired consecutive dark and light images can include same (or similar) background image content caused by reflected ambient light (e.g., reflected white light emitted by the light source 209*b* or by the light source 209*m* of the motherscope 115*m*, or spurious emitted fluorescence due to the white light from the light sources 209*m*, 209*b*) passing through the emission filter 233*b* (e.g., due to a non-ideal operation of the filter), thus reaching the sensing surface of the fluorescence image sensor 234*b*. However, this common background image content can be spatially misaligned within the consecutive acquired dark and light images, due to movement of objects within the captured scene and/or motion of the fluorescence camera 236*b* relative to the captured scene.

In order to solve this problem, the central unit 242*b* of the babyscope 115*b* is configured to perform motion-stabilized background subtraction on a sequence of alternated dark/light images asynchronously acquired relative to a sequence of color images by performing the previously disclosed method 300 of FIG. 3 during the use of the endoscopic system 500 in an endoscopic procedure (e.g., to inspect the target body region 109 as illustrated in FIG. 7).

In particular, after administrating a fluorescent substance to the patient, the endoscopic procedure may start. After a complete or partial anesthesia (if required), a physician inserts the probe of the motherscope 115*m*, switched on by a (healthcare) operator, into the cavity of the patient until its tip reaches the region of interest 109 of the patient body-part where a tumor (or other lesion) might be present. During operation, the white light source 209*m* of the motherscope 115*m* constantly illuminates the scene within the field of view 221*m*, and the color camera 239*m* is continually used to acquire motherscope color images of the illuminated scene that are displayed in real-time on the monitor 121*m* of the motherscope 115*m*.

At a certain point of the endoscopic procedure the physician inserts the probe of the babyscope 115*b* into a working channel of the motherscope 115*m*, until its tip reaches the same target region of interest 109 of the patient body-part (at the tip of the probe of the motherscope). During the insertion of the babyscope 115*b* along the working channel of the motherscope 115*m* or when the tip of the probe of the babyscope 115*b* has reached the tip of the probe of the motherscope 115*m* close to the target region of interest 109, the healthcare operator can enter a start command into the babyscope 115*b*. In response, the color imaging control module of the central unit 242*b* turns on the white light source 209*b* (that is preferably constantly maintained turned-on during the operation of the babyscope 115*b*) and starts controlling the acquisition, over the color channel, of a sequence of color images (including for example the color images 401-406 illustrated in FIG. 4) using the color camera 239*b*. The color imaging control module stores these color images in the dedicated repository (with the associated timestamps) as the sequence acquisition progresses.

While the color imaging control module of the babyscope 115*b* is controlling the acquisition of the sequence of color images over the color channel, the operation of the method 300 illustrated in FIG. 3 starts at step 301 with the fluorescence imaging control module of the babyscope 115*b* controlling the fluorescence camera 236*b* to acquire, over the fluorescence channel, a first fluorescence channel image (for example, the dark image 601 illustrated in FIG. 4).

Each of the following steps of the method 300 is respectively operated by the fluorescence imaging control module or the color imaging control module of the central unit 242*b* (or by any alternative module within the central unit 242*b* or by another unit of the babyscope 115*b* configured to perform the specific step), similarly to the previously disclosed operation of these steps by respectively the fluorescence imaging control module 281 or the color imaging control module 282 of the control unit 205 of the system 100 (or by any alternative module within the central unit 205 or other unit of the system 100 configured to perform the specific step).

These method steps are iteratively performed in relation to the sequence of acquired alternate light/dark fluorescence channel images, resulting in a sequence of background-subtracted fluorescence images being generated (with motion correction) over the fluorescence channel and displayed in succession on the monitor 121*b* of the babyscope 115*b* (overlaid on respective associated color images acquired over the color channel of the babyscope 115*b* and, possibly, on the color images concurrently acquired by the motherscope 115*m*) as a part of the displayed real-time video stream.

The method 300 continues in this way until at step 305 there is determined that there are no further fluorescence channel images to be acquired over the fluorescence channel (e.g., because the operation of the babyscope 115*b* is terminated and the operator has provided a stop command to the babyscope 115*b*). At this stage, at step 318 the method 300 ends.

Similarly to the system 100, in case of synchronously acquisitions of the sequence of color and alternating dark/light images (as illustrated for example in FIG. 5), the endoscopic system 500 can be configured to perform the method 300 illustrated in FIG. 3, but with the difference that the determination (at steps 304, 310) of a reference color image for a given acquired fluorescence channel image can be simply performed by selecting the color image whose acquisition is temporally aligned with the reference time of the given fluorescence channel image.

Further embodiments of the present disclosure provide a computer program, which is configured for causing a computing device of a medical fluorescence imaging system, such as the system 100 or the endoscopic system 500, to perform the above disclosed method 300 when the computer program is executed on the computing device. Further embodiments provide a computer program product, which comprises a computer readable storage medium embodying a computer program, the computer program being loadable into a working memory of a computing device of a medical fluorescence imaging system, thereby configuring the computing device to perform the same method. However, the computer program may be implemented as a stand-alone module, as a plug-in for a pre-existing software program (for example, a manager of the imaging system) or even directly in the latter. In any case, similar considerations apply if the computer program is structured in a different way, or if additional modules or functions are provided; likewise, the memory structures may be of other types, or may be replaced with equivalent entities (not necessarily consisting of physical storage media). The computer program may take any form suitable to be used by any computing device, thereby configuring the computing device to perform the desired operations. Particularly, the computer program may be in the form of external or resident software, firmware, or microcode (either in object code or in source code—for example, to be compiled or interpreted). Moreover, it is possible to provide the computer program on any computer readable storage medium. The storage medium is any tangible medium (different from transitory signals per se) that may retain and store instructions for use by the computing device. For example, the storage medium may be of the electronic, magnetic, optical, electromagnetic, infrared, or semiconductor type; examples of such storage medium are fixed disks (where the program may be pre-loaded), removable disks, memory keys (for example, of USB type), and the like. The computer program may be downloaded to the computing device from the storage medium or via a network (for example, the Internet, a wide area network and/or a local area network comprising transmission cables, optical fibers, wireless connections, network devices); one or more network adapters in the computing device receive the computer program from the network and forward it for storage into one or more storage devices of the computing device. In any case, the operation of the above-disclosed method 300 can be implemented even with a hardware structure (for example, by electronic circuits integrated in one or more chips of semiconductor material, such as a Field Programmable Gate Array (FPGA) or application-specific integrated circuits), or with a combination of software and hardware suitably programmed or otherwise configured.

MODIFICATIONS

Although this disclosure has been described with reference to particular embodiments of the present invention, it should be understood that various omissions, substitutions and changes in the form and details of the disclosed embodiments as well as other embodiments are possible.

For example, although in the disclosed systems 100 and 500 color cameras 250 and **239*b* are used, in cooperation with respective white light sources 215, 209*b*, to acquire sequences of color images 401-406 in addition to the fluorescence channel images acquired by the fluorescence cameras 245, 236*b*, it is to be noted that any other reflectance camera (i.e. a camera configured to acquire images in response to reflected light) can be used alternatively to or in combination with the color cameras 250, 230*b*** in order to acquire a sequence of reflectance images (that can be used to provide motion information for performing motion-stabilized background subtractions between the fluorescence channel images according to the embodiments of the present invention). For instance, the reflectance camera can include a simple image sensor that is not capable of separately detecting the intensity of separate color components of incoming reflected light, e.g., a CCD or CMOS sensor without CFA. In this case, the reflectance camera can generate monochrome (greyscale) images in response to detection by the sensor of reflected light. In other variations, a reflectance camera can be used, in cooperation with a light source configured to emit reflectance light different than visible light (but still not causing significant fluorescence phenomenon in an illuminated target body part with a fluorescent substance, and different than the fluorescent light emitted by the substance when excited—e.g., far IR or UV light, in case of using a fluorescent substance excitable with NIR light) to acquire reflectance images (e.g., IR or UV images) in response to detection of the reflected non-fluorescent light.

For example, although in the disclosed systems 100 and 500 two separate cameras 245, 250 and **236*b*, 29*b* having substantially a same field of view 104, 221*b* are used to acquire fluorescence and color images, respectively (with the aid of a beam-splitter 235, 236*b***), fluorescence and reflectance cameras having only a partially overlapping (or different) field of view may be used. In this case, post-image acquisition processing steps can be performed to align the field of view of the fluorescence channel and reflectance images.

Alternatively, a single camera can be used to acquire both color images (or any other reflectance images) and fluorescence channel images, in an asynchronous or synchronous way. For instance, a single reflectance+fluorescence camera can be used including an image sensor associated with a RGB+NIR filter (allowing, respectively, red, green and blue components of the incoming reflected visible light and emitted fluorescent light to reach respective filtered pixel areas of the sensor surface). In still further variations, the image sensor can comprise a hyperspectral sensor with separate planes sensitive to sub-bands of red, green or blue light or indeed separate bands of NIR light.

Moreover, it is to be noted that an imaging acquisition system according to the present invention may not include a white light source used to acquire the reflectance images (especially in case of an imaging acquisition system used in medical operations where the inspected body part is exposed to artificial light and/or sunlight illuminating the room where the medical operations are performed).

It is to be further noted that an imaging acquisition system according to the present invention may not include a reflectance camera in order to acquire the reflectance images used to perform motion-stabilized image subtraction on the images acquired by the fluorescence camera. In this case, the system can obtain the reflectance images from any external source connected to the system and configured to acquire reflectance images of the same scene imaged by the fluorescence camera.

Although the disclosed embodiments refer to the use of fluorescent substances excitable with NIR light and the corresponding use, in the systems 100 and 500, of NIR excitation light sources 210, **203*b*, and NIR-sensitive image sensors 241, 234*b***, the fluorescent substances used to mark a target body part can be excitable by light outside the NIR spectrum, e.g., within the UV spectrum or the far IR spectrum, or a part of the visible spectrum. In this case, corresponding suitable excitation lights (e.g., UV light or IR lights) are used, in cooperation with image sensors capable of sensing the fluorescent light emitted by the fluorescent object in response to the excitation light (e.g., in the UV or IR spectrum).

For example, although in the disclosed embodiments the white light sources 215, **209*m*, 209*b* are constantly maintained in an on-state during operation respectively of the system 100 and during operation of the motherscope 115***m* and the babyscope 115*b* of the endoscopic system 500, these white light sources can be controlled to be switched-off at least during the acquisition time of the fluorescence channel dark or light images.

Moreover, even if the endoscopic system 500 illustrated in FIG. 6 contains two separate central units 242*m*, 242*b* for the motherscope 115*m* and the babyscope 115*b*, respectively, a single central unit can be used to control the operation of both the motherscope 115*b* and the babyscope 115*m* (or at least some of the components of the units 242*m*, 242*b* can be shared between the motherscope 115*m* and the babyscope 115*b*).

With reference now to FIG. 4, although this figure illustrates a sequence of color images 401-406 acquired with a frequency twice than the frequency of acquisition of the asynchronous alternated dark/light images 601-603, the color image acquisition frequency can be greater than twice the fluorescence channel image acquisition frequency (resulting in more color images being acquired between the color image consecutive to the acquisition of a given fluorescence channel image and the color image preceding the acquisition of a next fluorescence channel image) or equal to the fluorescence channel image acquisition frequency (resulting in the color image consecutive to the acquisition of the given fluorescence channel image corresponding to the color image preceding the acquisition of the next fluorescence channel image).

Figure 5:
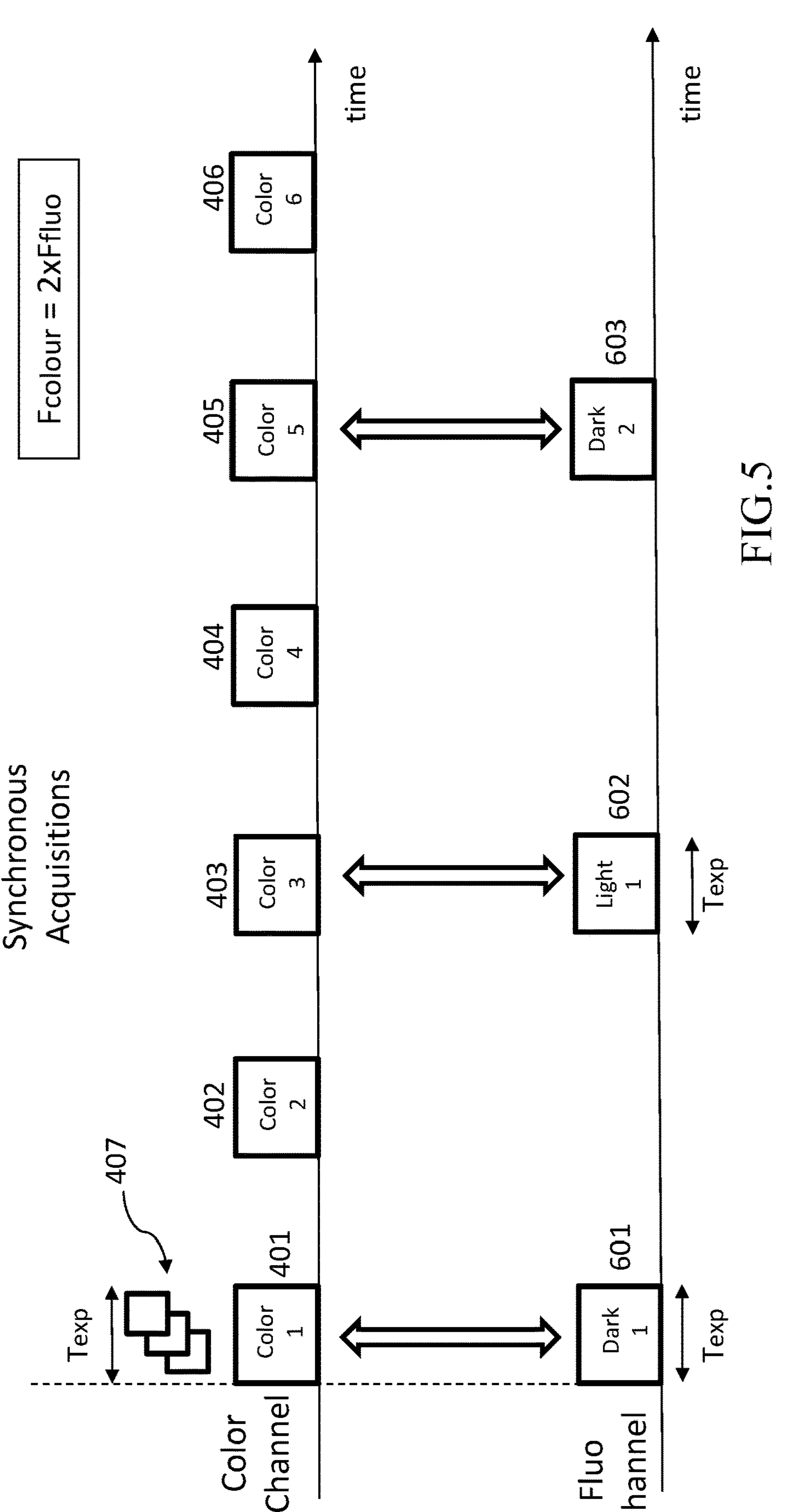
FIG. 5 illustrates a sequence of color images and dark and light images acquired synchronously over time, with reference color images assigned to the dark or light images according to an embodiment of the present invention.

Similarly, with reference now to FIG. 5, although this figure illustrates a sequence of color images 401-406 acquired with a frequency twice than the frequency of acquisition of the synchronous alternated dark/light images 601-603, the color image acquisition frequency can be greater than twice the fluorescence channel acquisition frequency (resulting in more color images being acquired between the color image at the acquisition of a given fluorescence channel image and the color image preceding the acquisition of a next fluorescence channel image) or equal to the fluorescence channel acquisition frequency (resulting in each color image being acquired at the acquisition time of a corresponding fluorescence channel image). Furthermore, the above disclosed principles of operation of the method 300 apply to embodiments where the reflectance image acquisition frequency is lower than the fluorescence channel image acquisition frequency.

Moreover, it is to be noted that the frequency of acquisition over the color and fluorescence channels can vary in different operations of a fluorescence imaging system according to the invention, or even during a same operation.

For example, although the operation of the method 300 has been disclosed above referring to the examples of FIGS. 4-5 (where the acquisition times of the color images 401-406 have substantially same duration as the exposure times used to acquire the light/dark images 601-603), the acquisition times of the reflectance images can be (even significantly) shorter than the acquisitions time of the dark/light images 601-603 (so as for example at least two reflectance images are acquired during the acquisition time of a corresponding light or dark fluorescence channel image). In this case, the reference time used to determine a reference reflectance image associated with a given fluorescence channel image may correspond to the middle time of the acquisition of the given fluorescence channel image.

With reference now to the method 300 illustrated in FIG. 3, and specifically to two of the above-disclosed solutions to determine and assign a color reference image to a given fluorescence channel image under analysis (at steps 304, 310), namely interpolation between the two acquired color images surrounding the given fluorescence channel image or selection of the closest in time of the two color images to the given fluorescence channel image, it is to be noted that although these solutions have been disclosed as alternative solutions, these solutions may be combined (for example, by selecting the closest of the two surrounding color images if it is close enough to the given fluorescence channel image, e.g., within a predetermined time interval, otherwise performing interpolation between the two surrounding color images to determine a virtual reference color image).

Moreover, although the displaying step 371 of the method 300 has been disclosed in relation to displaying the obtained sequence of motion-corrected background-subtracted images on the monitors 155,140, 121*b* of the systems 100, 500, the obtained sequence may be alternatively or in addition be outputted (e.g., wirelessly) for displaying on an external device connected to the systems 100, 500 (e.g., virtual reality glasses, a smart TV or room screen, and the like). With reference to the operation of the method 300 by the endoscopic system 500 illustrated in FIGS. 6-7, a sequence of color images acquired by the motherscope 115*m* may be used, in alternative or in addition, to the sequence of color images acquired by the babyscope 115*b* in order to perform background subtraction with motion correction on the sequence of alternate dark/light fluorescence channel images acquired by the motherscope 115*m* as per the above-disclosed operation of the method 300.

Moreover, it is to be noted that even if the above disclosed system 500 includes the motherscope 115*m* and the babyscope 115*b*, the method 300 can be also performed by an endoscope system with only one scope (including at least a fluorescence camera).

Moreover, it is to be noted that the method 300 has been disclosed only as an exemplary embodiment for performing motion-corrected background subtraction, and other modification may apply to the disclosed method 300 (by using similar steps with the same functions of more steps or portions thereof, removing some steps being non-essential, or adding further optional steps); moreover, the steps of the method 300 or any modified version may be performed in a different order, concurrently or in an interleaved way (at least in part).

Although the operation of a method for performing motion-stabilized background subtraction according to the present invention has been disclosed in relation to the systems 100 and 500 in use for a surgical operation and an endoscopic operation, respectively, it is to be noted that the method can be also advantageously operated in other systems/apparatus using fluorescence imaging for other medical (e.g., surgical/diagnostic/therapeutic) or cosmetic applications requiring inspection of a target body part.

For example, an embodiment provides a surgical method comprising the following steps. A body-part of the patient is imaged according to the above-disclosed method according to the present disclosure, thereby displaying a sequence of motion-stabilized background-subtracted fluorescence images. The body-part is operated according to said displaying this sequence of images. However, the proposed method may find application in any kind of surgical method in the broadest meaning of the term (for example, for curative purposes, for prevention purposes, for aesthetic/cosmetic purposes, and so on) and for operating any kind of body-part of any patient.

A further embodiment provides a diagnostic method comprising the following steps. A body-part of the patient is imaged according to the above-disclosed method according to the present disclosure, thereby displaying a sequence of motion-stabilized background-subtracted fluorescence images. The body-part is analyzed according to the displayed sequence of images. However, the proposed method may find application in any kind of diagnostic applications in the broadest meaning of the term (for example, aimed at evaluating health conditions, discovering new lesions, monitoring known lesions, and so on) and for analyzing any kind of body-part of any patient (see above).

An embodiment provides a therapeutic method comprising the following steps. A body-part of the patient is imaged according to the above-disclosed method according to the present disclosure, thereby displaying a sequence of motion-stabilized background-subtracted fluorescence images. The body-part is treated according to the displayed sequence of images. However, the proposed method may find application in any kind of therapeutic method in the broadest meaning of the term (for example, aimed at curing a pathological condition, at avoiding its progress, at preventing the occurrence of a pathological condition, or simply at ameliorating a comfort of the patient) and for treating any kind of body-part of any patient (see above).

In any case, although the method may facilitate the task of a physician, it only provides intermediate results that may help him/her, but with the medical activity stricto sensu that is always made by the physician himself/herself; moreover, the body-part may be of any type (for example, organs, such as liver, prostate or heart, regions, tissues and so on), in any condition (for example, within a living being, within a dead body, extracted from a body, such as a sample of a biopsy, and so on) and of any patient (for example, a human being, an animal, and so on). The target of the procedure is defined by a target condition of the body-part. However, the target condition may be of any type (for example, any pathological tissue such as tumor, inflammation and the like, healthy tissue and so on).

The fluorescent substance used to image the target body-part may be of any extrinsic/intrinsic or exogenous/endogenous type (for example, any fluorescent agent, any natural fluorescence component, and so on). As such, the fluorescent agent may be administered in any way (e.g., in a non-invasive manner, for example, orally for imaging the gastrointestinal tract, via a nebulizer into the airways, via topical spray application or topical introduction during a surgical procedure, and so on, or in any case without any substantial physical intervention on the patient that would require professional medical expertise or entail any health risk for the patient, e.g., intramuscularly) and at any time (for example, in advance, immediately before performing the method, continuously during it, and so on), or this step may be omitted at all (in case the agent is endogenous). Furthermore, the fluorescent agent can circulate in the target body-part (rather than attaching to some biological components of the body-part).

Moreover, it is expressly intended that specific features and/or method steps described in connection with any embodiment of the present disclosure may be incorporated in any other embodiment as a matter of general design choice. Moreover, items presented in a same group and different embodiments, examples or alternatives are not to be construed as de facto equivalent to each other (but they are separate and autonomous entities).

The invention claimed is:

1. A method for motion-stabilized image background subtraction in an imaging acquisition system for imaging a scene including at least one target body-part containing a fluorescent substance, wherein the imaging acquisition system includes:

a light source configured to emit excitation light to illuminate the target body-part, the excitation light being suitable for causing emission of fluorescent light from the target body-part; and a fluorescence camera having a fluorescence emission detection passband configured to allow detection of the fluorescent light emitted by the target body-part;

and the method comprising:

obtaining a sequence of reflectance images acquired by a reflectance camera configured to detect reflected light due to an illumination condition different than the excitation light;

while obtaining the sequence of reflectance images, acquiring, using the fluorescence camera, a sequence of fluorescence channel images including light images, acquired while using the light source to cause the target body-part to emit fluorescent light, alternating with dark images, acquired without using the light source to cause the target body-part to emit fluorescent light;

determining a first reflectance image of said sequence of reflectance images associated with a first fluorescence channel image, the first fluorescence channel image having a first reference time;

determining a second reflectance image of said sequence of reflectance images associated with a second fluorescence channel image acquired by the fluorescence camera consecutively to the first fluorescence channel image, the second fluorescence channel image having a second reference time;

determining a transformation matrix based on a relative alignment of the first and second reflectance images;

applying the transformation matrix to one of the first and second fluorescence channel images to align the first and second fluorescence channel images;

performing a subtraction between said one of the first and second fluorescence channel images to which the transformation matrix has been applied and the other of the first and second fluorescence channel images to obtain a background-subtracted image; and outputting the background-subtracted image for displaying.

2. The method of claim 1, wherein said first reference time is between the acquisition of the first reflectance image and the acquisition of an adjacent third reflectance image, wherein said second reference time is between the acquisition of the second reflectance image and the acquisition of an adjacent fourth reflectance image, and wherein said determining the transformation matrix comprises:

determining a first interpolated transformation matrix to align the first reflectance image to the first fluorescence channel image using the third reflectance image; and determining a second interpolated transformation matrix to align the second reflectance image to the second fluorescence channel image using the fourth reflectance image.

3. The method of claim 2, wherein said determining the first interpolated transformation matrix comprises:

calculating a first interpolation factor between the first and third reflectance images as function of relative acquisition times of the first and third reflectance images and said first reference time;

determining a first transformation matrix to align the first and third reflectance images; and applying the first interpolation factor to the first transformation matrix to obtain the first interpolated transformation matrix;

and wherein said determining the second interpolated transformation matrix comprises:

calculating a second interpolation factor between the second and fourth reflectance images as a function of the relative acquisition times of the second and fourth reflectance images and said second reference time;

determining a second transformation matrix to align the second and fourth reflectance images; and applying the second interpolation factor to the second transformation matrix to obtain the second interpolated transformation matrix.

4. The method of claim 3, where said applying the first interpolation factor to the first transformation matrix comprises:

decomposing the first transformation matrix into motion components;

applying the first interpolation factor to the motion components; and reassembling the first transformation matrix from the interpolated motion components to obtain the first interpolated transformation matrix; and wherein said applying the second interpolation factor to the second transformation matrix comprises:

decomposing the second transformation matrix into motion components;

applying the second interpolating factor to the motion components; and reassembling the second transformation matrix from the interpolated motion components to obtain the second interpolated transformation matrix.

5. The method of claim 3, wherein said applying the first interpolation factor to the first transformation matrix comprises:

determining a fractional power of the first transformation matrix corresponding to the first interpolation factor; and wherein said applying the second interpolation factor to the second transformation matrix comprises:

determining a fractional power of the second transformation matrix corresponding to the second interpolation factor.

6. The method of claim 2, comprising determining the transformation matrix as a function of the first and second reflectance images and the first and second interpolated transformation matrices.

7. The method claim 2, comprising determining the transformation matrix by:

applying the first interpolated transformation matrix to the first reflectance image to obtain a first virtual reflectance image approximatively aligned to the first fluorescence channel image;

applying the second interpolated transformation matrix to the second reflectance image to obtain a second virtual reflectance image approximatively aligned to the second fluorescence channel image; and determining a transformation matrix to align the first and second virtual reflectance images.

8. The method of claim 2, comprising determining the transformation matrix by:

applying the first interpolated transformation matrix to align the first fluorescence channel image to the first reflectance image;

applying the second interpolated transformation matrix to align the second fluorescence channel image to the second reflectance image; and determining a transformation matrix to align the first and second reflectance images.

9. The method of claim 1, wherein said determining the first reflectance image includes:

selecting a reflectance image acquired closest in time to said first reference time; and wherein said determining the second reflectance image comprises:

selecting a reflectance image acquired closest in time to said second reference time; and wherein the method comprises determining the transformation matrix by:

determining a transformation matrix to align the selected first and second reflectance images.

10. The method of claim 1, wherein the reflectance images are acquired at respective times corresponding to reference times during the acquisitions of corresponding fluorescence channel images.

11. The method of claim 1, wherein the reflectance images are acquired at a frequency greater to or equal than the fluorescence channel images.

12. The method of claim 1, wherein said imaging acquisition system further comprises:

the reflectance camera;

and wherein said obtaining a sequence of reflectance images comprises:

acquiring, using the reflectance camera, said sequence of reflectance images.

13. The method of claim 12, wherein the reflectance camera has a field of view substantially overlapping the field of view of the fluorescence camera.

14. The method of claim 1, wherein said acquiring the sequence of reflectance images comprises acquiring the first reflectance image by:

acquiring a plurality of first reflectance frames over a time period having a duration corresponding to an exposure time used to acquire the first fluorescence channel image; and combining together the first reflectance frames to form a single acquired reflectance image; and acquiring the second reflectance images by:

acquiring a plurality of second reflectance frames over a time period having a duration corresponding to an exposure time used to acquire the second fluorescence channel image; and combining together the second reflectance frames to form a single acquired reflectance image.

15. The method of claim 1, further comprising:

determining whether either the first fluorescence channel image or the second fluorescence channel image is overexposed; and in response to determining that either the first fluorescence channel image or the second fluorescence channel image is overexposed, outputting a warning of excessive ambient light.

16. The method of claim 1, further comprising:

determining whether a motion estimated by the transformation matrix to align the first and second fluorescence channel images is above a threshold, and in response to determining that the estimated motion is above the threshold, outputting a warning of excessive motion.

17. The method of claim 1, wherein:

the method is performed to image at least one target body-part of a patient; and the method further comprising operating the target body-part according to said displaying the background-subtracted fluorescence.

18. The method of claim 1, wherein:

the method is performed to image at least one target body-part of a patient; and the method further comprising analyzing the target body-part according to said displaying the background-subtracted fluorescence.

19. The method of claim 1, wherein:

the method is performed to image at least one target body-part of a patient; and the method further comprising treating the body-part according to said displaying the background-subtracted fluorescence.

20. An imaging acquisition system for imaging a scene including at least one target body-part containing a fluorescent substance, the imaging acquisition system comprising:

a light source configured to emit excitation light to illuminate the at least one target body-part, the excitation light being suitable for causing emission of fluorescent light from the target body-part; and a fluorescence camera having a fluorescence emission detection passband configured to allow detection of the fluorescent light emitted by the target body part;

the imaging acquisition system being configured to:

obtain a sequence of reflectance images acquired by a reflectance camera configured to detect reflected light due to an illumination condition different than the excitation light;

while obtaining the sequence of reflectance images, acquire, using the fluorescence camera, a sequence of fluorescence channel images including light images, acquired while using the light source to cause the target body-part to emit fluorescent light, alternating with dark images, acquired without using the light source to cause the target body-part to emit fluorescent light;

determine a first reflectance image of said sequence of reflectance images associated with a first fluorescence channel image, the first fluorescence channel image having a first reference time;

determine a second reflectance image of said sequence of reflectance images associated with a second fluorescence channel image acquired by the fluorescence camera consecutively to the first fluorescence channel image, the second fluorescence channel image having a second reference time;

determine a transformation matrix based on a relative alignment of the first and second reflectance images;

apply the transformation matrix to one of the first and second fluorescence channel images to align the first and second fluorescence channel images;

perform a subtraction between said one of the first and second fluorescence channel images to which the transformation matrix has been applied and the other of the first and second fluorescence channel images to obtain a background-subtracted image; and output the background-subtracted image for displaying.

21. A computer program product comprising a non-transitory computer readable storage medium including computer instructions wherein, when a computing device of an imaging acquisition system executes the computer instructions of the non-transitory computer readable medium, the computer instructions executed by the computer device result in the computer device causing the imaging acquisition system to:

obtain a sequence of reflectance images acquired by a reflectance camera configured to detect reflected light due to an illumination condition different than the excitation light;

while obtaining the sequence of reflectance images, acquiring, using the fluorescence camera, a sequence of fluorescence channel images including light images, acquired while using the light source to cause the target body-part to emit fluorescent light, alternate with dark images, acquired without using the light source to cause the target body-part to emit fluorescent light;

determine a first reflectance image of said sequence of reflectance images associated with a first fluorescence channel image, the first fluorescence channel image having a first reference time;

determine a second reflectance image of said sequence of reflectance images associated with a second fluorescence channel image acquired by the fluorescence camera consecutively to the first fluorescence channel image, the second fluorescence channel image having a second reference time;

determine a transformation matrix based on a relative alignment of the first and second reflectance images;

apply the transformation matrix to one of the first and second fluorescence channel images to align the first and second fluorescence channel images;

perform a subtraction between said one of the first and second fluorescence channel images to which the transformation matrix has been applied and the other of the first and second fluorescence channel images to obtain a background-subtracted image; and output the background-subtracted image for displaying.

* * * * *